(12) United States Patent
Sun et al.

(10) Patent No.: US 7,973,014 B2
(45) Date of Patent: Jul. 5, 2011

(54) MEDICINAL COMPOSITION CONTAINING GINSENG SECONDARY GLYCOSIDES, ITS PREPARATION METHOD AND APPLICATION

(75) Inventors: Congxin Sun, Beijing (CN); Hesheng Luo, Beijing (CN); Yongli Zhao, Beijing (CN)

(73) Assignee: National Institute of Pharmaceutical R&D Co., Ltd., Beijing (CN)

( * ) Notice: Subject to any disclaimer, the term of this patent is extended or adjusted under 35 U.S.C. 154(b) by 602 days.

(21) Appl. No.: 11/995,320

(22) PCT Filed: Jul. 5, 2006

(86) PCT No.: PCT/CN2006/001574
§ 371 (c)(1),
(2), (4) Date: Jan. 11, 2008

(87) PCT Pub. No.: WO2007/006208
PCT Pub. Date: Jan. 18, 2007

(65) Prior Publication Data
US 2008/0234208 A1    Sep. 25, 2008

(30) Foreign Application Priority Data

Jul. 14, 2005 (CN) .......................... 2005 1 0083852
Jul. 14, 2005 (CN) .......................... 2005 1 0083854
Jul. 14, 2005 (CN) .......................... 2005 1 0083855

(51) Int. Cl.
*A61K 31/70* (2006.01)
(52) U.S. Cl. ........................................ 514/26; 514/25
(58) Field of Classification Search ............. 514/26
See application file for complete search history.

(56) References Cited

U.S. PATENT DOCUMENTS

| 7,438,935 B2 * | 10/2008 | Wei et al. ............... 424/728 |
| 2004/0247703 A1 | 12/2004 | Rhim et al. |
| 2005/0113316 A1 | 5/2005 | Huang et al. |

FOREIGN PATENT DOCUMENTS

| CA | 2 436 469 A1 | 1/2004 |
| CN | 1156281 | 8/1997 |
| CN | 1193038 | 9/1998 |
| CN | 1092204 | 2/2000 |
| CN | 1092204 | 10/2002 |
| CN | 1498622 | 5/2004 |
| CN | 1156281 | 7/2004 |
| CN | 1569011 | 1/2005 |
| CN | 1193038 | 3/2005 |
| CN | 1586589 | 3/2005 |
| CN | 1593442 | 3/2005 |

OTHER PUBLICATIONS

Kim et al, Arch. Pharm. Res. vol. 27, No. 4, (2004), pp. 429-435.*
Radad et al, Iranian Journal of Pharmacology & Therapeutics, vol. 3, No. 2, (2004), pp. 30-40.*
International Search Report from corresponding International Application No. PCT/CN2006/001574.
Canadian Office Action dated Mar. 8, 2010 from corresponding Canadian Application No. 2,617,700.

* cited by examiner

*Primary Examiner* — Elli Peselev
(74) *Attorney, Agent, or Firm* — Wolf, Greenfield & Sacks, P.C.

(57) ABSTRACT

Medicinal composition containing ginseng secondary glycosides, its preparation method and application. The present composition contains mainly, as active ingredients, the ginsenoside with protopanoxadiol as aglucone (ginsenoside Rg3) and the ginsenoside with protopanoxatriol as aglucone (ginsenoside Rg2 and ginsenoside Rh1). It is prepared from the ginseng genus of plants through extracting, acid hydrolyzing and using macroreticular resin to separate, purify and concentrate. It is useful in the manufacture of medicaments for treating CHD, angina pectoris, myocardial ischemia, hemorrhagic shock, heart failure, and arrhythmia.

10 Claims, No Drawings

MEDICINAL COMPOSITION CONTAINING GINSENG SECONDARY GLYCOSIDES, ITS PREPARATION METHOD AND APPLICATION

FIELD OF INVENTION

The present invention relates to a pharmaceutical composition and its preparation process and use, in particular to a pharmaceutical composition containing total secondary ginsenosides of Radix ginseng as well as its preparation and use.

BACKGROUND OF THE INVENTION

Radix Ginseng is one of the most important drugs for qi supplementation in traditional Chinese medicine. Its taste and nature: sweet and slightly bitter in taste and neutral in nature. Its functions and indications: having effects of replenishing the vital qi, restoring pulse and relieving collapse syndrome, reinforcing the spleen and lung, promoting the production of body fluid and tranquilizing the mind. Its indications: prostration due to general deficiency, cold extremities and faint pulse, poor appetite due to deficiency of the spleen, asthma due to deficiency of the lung, thirst due to impairment of body fluid, diabetes due to interior heat, general weakness due to prolonged illness, palpitation, insomnia, impotence, uterine coldness, heart failure and cardiogenic shock.

Clinical practices in traditional Chinese medicine and its combination with western medicine have confirmed that ginseng and preparations thereof had pharmacological activities for enhancing myocardial contraction force, expanding coronary artery, increasing coronary artery blood flow, reducing myocardial oxygen consumption, protecting heart muscle from reperfusion injury, inhibiting platelet aggregation, acting as antithrombin, etc., and are clinically used for treatment of chest impediment and heart pain (coronary heart disease), arteriosclerosis, etc.

The main reasons for chest impediment (thoracic obstruction) and heart pain are "YANG QI is weakened and does not run well in chest, and after a long time, YIN QI subjugates YANG QI, thereby forming obstruction" ("Classification and Treatment of Symptoms —Chest Impediment Chapter), or "pathogenic cold attacks body, cold food is eaten, heat accumulates in the interior, obstinate phlegm and dead blood exist for a long time, or because rage causes adverseness of QI" ("Ancient and Modern Medicine—Heart Pain Section).

When a person is middle-aged, chest impediment and heart pain may be caused by physical deterioration, gradual weakness of five solid organs, the disorder of functions of ZANG FU organs, deficiency of YANG QI in body, pathogenic hot or cold QI attacking the body, or eating and drinking without temperance, preference for fat and sweet food, or anxiety and overstrain, or depressed emotion. The pathogenic focus is heart, relating to lung, spleen, liver and kidney. Pathological changes are imbalance of YIN and YANG in ZANG FU and QI-blood, deficiency of heart-blood, deficiency of heart-YANG, thereby resulting in stagnation of QI, cold accumulation, phlegm, congestion, etc. that may stagnate heart meridian so that the impeded heart meridian, stagnated QI and blood stasis cause disease. The underlying pathogenesis is asthenia in origin and sthenia in superficiality, wherein asthenia in origin is deficiency of heart qi, heart blood, heart yin or heart-kidney YANG, while sthenia in superficiality is stagnation of QI, cold accumulation, phlegm, congestion that may stagnate heart meridian. During the pathogenesis, asthenia in origin and sthenia in superficiality usually are causes and results mutually and aggravate pathological condition, thereby presenting complicated symptoms with both appearance and substance. The treatment thereof mainly relates to harmonization of YIN and YANG, pyretic tonification of YANG-QI, and promoting flow of QI and blood. QI masters blood, so that blood circulation depends on QI flow. It is an important rule in treatment of chest impediment and heart pain to invigorate QI and enhearten YANG, and to activate blood circulation and dissipate blood stasis.

The results of researches in modern science indicate that the main bioactive components of Radix ginseng are ginsenosides. Although both red ginseng and sun-dried ginseng contain ginsenosides, their ginsenosides are different, i.e., red ginseng contains some ginsenosides such as ginsenosides Rg2, Rg3, Rh1, Rh2, etc. that do not exist in sun-dried ginseng. These new ginsenosides are secondary ginsenosides generated by hydrolysis of ginsenosides during the procedure for processing ginseng, such as steaming and drying steps.

These secondary ginsenosides have many new activities, for example, ginsenosides Rh1, Rh2 and Rg3 have significant anticancer activity and are able to induce the redifferentiation of cancer cells, i.e., to induce cancer cells to redifferentiate into healthy cells, while other ginsenosides have not such effects or their effects are relatively weak. Ginsenoside Rg3 exhibits relatively strong inhibitory effects on the platelet aggregation induced by collagen or ADP. Ginsenoside Rh1 has significant inhibitory effects on the conversion of fibrinogen to fibrin induced by thrombin.

In addition, the in vivo metabolism of ginsenosides has been studied through serum pharmacology. The results show that native ginsenosides have a very low absorption rate in human body (e.g., the absorption rate of ginsenoside-Rb1 by oral administration is only 1%), and the active components actually absorbed by human body are secondary ginsenosides produced through the metabolism of intestinal bacteria. During the studying of in vivo metabolism of ginsenosides, Professor Wang Benxiang found that after oral administration of ginsenoside-Rg1, the bioactive components that were absorbed into blood were mainly secondary ginsenoside Rh1 produced by the metabolism of intestinal bacteria.

During the studying of the active components in "Pulse Engendering Beverage (Shengmaiyin)", Professor Yan Yongqing found that better therapeutic effects were obtained when all the ingredients of "Pulse Engendering Beverage (Shengmaiyin)" compound formula were boiled together than that achieved when these ingredients were boiled individually. After all the ingredients of the compound formula were boiled together, the ginsenosides in the beverage were mainly secondary ginsenosides Rg2, Rg3, and Rh1, and all the native ginsenosides disappeared. The results of this studying showed that the main active components in "Pulse Engendering Beverage (Shengmaiyin)" complex were ginsenosides Rg2, Rg3 and Rh1.

However, the natural contents of these ginsenosides are very low. For example, Rg3 is only 0.0003% in white ginseng, about 0.03% in red ginseng is, while Rh2 and C-K are not present in natural ginseng at all, and Rh2 is only about 0.001% in red ginseng. C-K are metabolic products of ginsenosides by intestinal bacteria. Since these ginseng secondary ginsenosides are very difficult to obtain, it is almost impossible to perform drug development that needs an amount of compound at several kilograms level. Thus, it is necessary to develop novel processes for the production of these compounds.

SUMMARY OF THE INVENTION

One object of the present invention is to provide a pharmaceutical composition containing secondary ginsenosides in order to overcome the drawbacks that native ginsenosides have very low absorption rate and relatively weak bioactivity in human body.

One object of the present invention is achieved as follows:

A pharmaceutical composition, comprising total secondary ginsenosides which is an extract of total secondary ginsenosides extracted from a plant of Radix ginseng; The said extract of total secondary ginsenosides comprise the following components:

(1) Ginsenosides with protopanaxadiol as aglycone, including ginsenoside-Rg3;
(2) Ginsenosides with protopanaxatriol as aglycone, including ginsenoside-Rg2 and ginsenoside-Rh1;

The sum of the ginsenosides with protopanaxadiol or protopanaxatriol as aglycone is 20%~98% by weight.

As for the extract of total secondary ginsenosides according to the present invention, its color and composition varies depending on the process for preparing total secondary ginsenosides and the content of total secondary ginsenosides in the extract, i.e., as the said content increases from 20% to 98% (the term "total secondary ginsenosides" used herein is identical to "the sum of the ginsenosides with protopanaxadiol or protopanaxatriol as aglycone" as mentioned above), the content of components other than the total secondary ginsenosides decreases gradually. After the extract from Radix ginseng plant is hydrolyzed with an organic acid and then directly concentrated to dryness, the obtained extract of total secondary ginsenosides is dark brown, in which the content of total secondary ginsenosides is 20%-40%, and the residual 60%-80% comprises polysaccharides, plant pigments, flavones and glycosides thereof, steroids and glycosides thereof;

After the extract from Radix ginseng plant is hydrolyzed with an organic acid, the hydrolyte liquid is extracted with an organic solvent, then the organic phase can be concentrated until dry to obtain an extract of total secondary ginsenosides; or the hydrolyte liquid can be absorbed by passing through a macroporous resin, washed with water to almost colorless, then eluted with an aqueous organic solvent or a pure organic solvent, the eluted portion containing organic solvent is concentrated until dry to obtain an extract of total secondary ginsenosides with a color of yellow, the content of total secondary ginsenosides therein being 40%-55%, and the residual 45%-60% comprising plant pigments, flavones and glycosides thereof, steroids and glycosides thereof;

After the extract from Radix ginseng plant is hydrolyzed with an organic acid, the hydrolyte liquid is extracted with an organic solvent. Then the organic phase is washed with an alkaline aqueous solution to remove the phenolic acid portion, and then the organic phase is concentrated until dry to obtain an extract of total secondary ginsenosides; or the hydrolyte liquid is absorbed by passing through a macroporous resin, washed with an alkaline aqueous solution to remove the portion of phenolic acid, washed with water until neutral and almost colorless, then eluted with a water-containing organic solvent or a pure organic solvent. The eluted portion containing organic solvent is concentrated until dry to obtain an extract of total secondary ginsenosides with a color of light yellow, the content of total secondary ginsenosides therein being 50%-70%, and the residual 30%-50% comprising plant pigments, steroids and glycosides thereof;

After the extract from Radix ginseng plant is hydrolyzed with an organic acid, the hydrolyte liquid is extracted with an organic solvent, the organic phase is washed with an alkaline aqueous solution to remove the portion of phenolic acid, and then the organic phase is concentrated until dry to obtain an extract of total secondary ginsenosides; or the hydrolyte liquid is absorbed by passing through a macroporous resin, washed with an alkaline aqueous solution to remove the phenolic acid portion, washed with water until neutral and almost colorless, then eluted with a water-containing organic solvent or a pure organic solvent, the eluted portion containing organic solvent is concentrated until dry to obtain an extract of total secondary ginsenosides. Such an extract of total secondary ginsenosides is separated by chromatography using a silica gel column, and detected by silica gel thin layer chromatography. The portions containing ginsenoside-Rg3, ginsenoside-Rg2 or ginsenoside-Rh1 are pooled, the mobile phase is evaporated to obtain an extract of total secondary ginsenosides with a white-like color. The content of total secondary ginsenosides therein is 70%-98%, and the residual 2%-30% comprises mainly steroids and glycosides thereof.

In a preferred embodiment, the said ginsenosides with protopanaxadiol as aglycone further include ginsenoside Rh2; and the said ginsenosides with protopanaxatriol as aglycone further include ginsenoside Rh3, ginsenoside Rf, Noto-ginsenoside R2;

the sum of ginsenosides with protopanaxadiol or protopanaxatriol as aglycone is 20%-98% by weight.

In a preferred embodiment, the said ginsenoside Rg3 is ginsenoside 20-(S)-Rg3 and/or ginsenoside 20-(R)-Rg3; the said ginsenoside Rg2 is ginsenoside 20-(S)-Rg2 and/or ginsenoside 20-(R)-Rg2; the said ginsenoside Rh1 is ginsenoside 20-(S)-Rh1 and/or ginsenoside 20-(R)-Rh1;

the said ginsenoside Rg3 is 10-30%, the said ginsenoside Rg2 is 1-20%, and the said ginsenoside Rh1 is 1-10%, expressed in weight percentage;

the sum of ginsenosides with protopanaxadiol or protopanaxatriol as aglycone is 50%-98%, expressed in weight percentage.

In a preferred embodiment, in the said pharmaceutical composition of total secondary ginsenosides, the said ginsenoside Rg3 is 12-20%, the said ginsenoside Rg2 is 4-16%, and the said ginsenoside Rh1 is 3-5%;

the sum of ginsenosides with protopanaxadiol or protopanaxatriol as aglycone is 50%-98% by weight.

The said plants for extracting total secondary ginsenosides are plants of *Panax*, including various ginsengs, American ginsengs, notoginseng, greater ginseng, preferably fibrous ginseng root.

The process for preparing the said pharmaceutical composition of total secondary ginsenosides by extraction comprises a hydrolysis step, wherein in the hydrolysis step, an inorganic acid or an organic acid is used as hydrolysis catalyst, preferably, acetic acid is used as the hydrolysis catalyst.

In a specific embodiment, the said pharmaceutical composition may comprise a therapeutically effective amount of the extract of total secondary ginsenosides, an additive, an excipient and a pharmaceutically acceptable carrier.

The pharmaceutical composition of total secondary ginsenosides according to the present invention is a preparation of total secondary ginsenosides obtained by hydrolyzing an extract of ginseng with a weak acid. The derivation of its main components is as follows: ginsenoside Rg3 (secondary ginsenoside) is produced by the hydrolysis of ginsenoside Rb group (native ginsenosides), ginsenoside Rg2 (secondary ginsenoside) is produced by the hydrolysis of ginsenoside Re group (native ginsenosides), and ginsenoside Rh1 (secondary ginsenoside) is produced by the hydrolysis of ginsenoside Rg1 group (native ginsenoside). After series of researches, we had determined optimal conditions for the gradient elution in high pressure liquid chromatography, under which 20-(S)-Rg3, 20-(R)-Rg3, 20-(S)-Rg2, 20-(R)-Rg2, 20-(S)-Rh1, 20-(R)-Rh1 of the present invention can be isolated very well.

A second object of the present invention is to provide a process for preparing a pharmaceutical composition of total secondary ginsenosides.

This object is achieved as follows:

A process for preparing a pharmaceutical composition of total secondary ginsenosides, comprising the following steps:
(1) Preparation of an extract liquid of total ginsenosides: extracting a plant of *Panax* with water or an organic solvent, then concentrating the resulting extract liquid;
(2) Preparation of hydrolyzate liquid: hydrolyzing the above concentrated extract liquid in the presence of an inorganic or organic acid as catalyst;
(3) Absorption with resin: passing the hydrolyzate liquid through a macroporous resin for absorption on column;
(4) Removal of impurities: eluting the absorption column that has absorbed the hydrolyzate liquid with water, an alkaline aqueous solution, and ethanol at a concentration below 35% to remove impurities;
(5) Elution, concentration, drying: after the removal of impurities, eluting the absorption column with ethanol at a concentration of above 35%, collecting the eluent being eluted with ethanol at a concentration of above 35%, concentrating the eluent to obtain a liquid extract, and drying under vacuum to obtain a pharmaceutical composition of total secondary ginsenosides.

In a preferred embodiment of the present invention, the inorganic or organic acid catalyst used in the said step (2) is selected from the group consisting of glacial acetic acid, propionic acid, hydrochloric acid, and sulfuric acid; the said hydrolysis is performed at 80-100° C. for 3-8 hours; and preferably, the hydrolysis is performed in the presence of glacial acetic acid at 99° C. for 5 hours.

In a further preferred embodiment, the macroporous resin being used in the step (3) is a styrene type macroporous resin, which is selected from the group consisting of styrene type macroporous resins, ethyl-styrene type macroporous resins, and methyl-styrene type macroporous resins.

In a further preferred embodiment, the alkaline aqueous solution used in the step (4) is an aqueous solution of a compound being selected from the group consisting of sodium hydroxide, potassium hydroxide, sodium carbonate, and potassium carbonate at a concentration of 0.1-5.0%. Preferably, sodium hydroxide is 0.3-0.7%, potassium hydroxide is 0.4-0.8%, sodium carbonate or potassium carbonate is 0.6-1.5%.

In a further preferred embodiment, the ethanol used in the step (4) for removal of impurities has a concentration of 15-25%.

In a still further preferred embodiment, the ethanol used for eluting the absorption column in the step (5) has a concentration of 60-80%.

A third object of the present invention is to provide a pharmaceutical preparation of extract of total secondary ginsenosides in various different dosage forms depending on different clinical applications and different conditions of patients.

For patients under normal conditions, the extract of total secondary ginsenosides can be formulated as oral disintegrating tablets, tablets, capsules, granules, oral liquid, drop pills, injections, etc, for administration.

During the preparation of tablets of total secondary ginsenosides, a powder of extract of total secondary ginsenosides, peppermint essence, sodium cyclamate, micro-powder silica gel, talc powder, etc. are used, and the tablets are prepared according to a conventional process. The extract of total secondary ginsenosides is 3%-85% based on the total weight of the tablet.

During the preparation of granules of total secondary ginsenosides, an extract of total secondary ginsenosides, starch, peppermint essence, sweeting agent, micro-powder silica gel, talc powder, etc. can be used, and the granules prepared according to a conventional process. The extract of total secondary ginsenosides is 3%-85% based on the total weight of the whole granule.

During the preparation of an oral liquid of total secondary ginsenosides, an extract of total secondary ginsenosides, Tween, sodium cyclamate, micro-powder silica gel, ethyl hydroxybenzoate, propyl hydroxybenzoate, etc. are used according to a conventional process. The extract of total secondary ginsenosides is 3%-85% based on the total weight of the whole oral liquid.

During the preparation of capsules of total secondary ginsenosides, an extract of total secondary ginsenosides, starch, micro-powder silica gel, talc powder, hollow hard capsules, etc. are used, and the capsules be prepared according to a conventional process. The extract of total secondary ginsenosides is 3%-85% based on the total weight of the whole capsule.

The present invention further provides oral disintegrating tablets of total secondary ginsenosides. This object is achieved as follows:

An oral disintegrating tablet of total secondary ginsenosides, which comprises the following components:
A) the aforementioned pharmaceutical composition of total secondary ginsenosides as the active ingredient;
B) an auxiliary component, including a filling agent; wherein
the components A) is 3%-85% based on the weight of the whole oral disintegrating tablet.

In a preferred embodiment, the auxiliary component B) in the oral disintegrating tablet of total secondary ginsenosides comprises a clathrate made from a masking agent or a solid dispersion.

In a preferred embodiment, the said filling agent used in the auxiliary components B) is one or more selected from the group consisting of starch, dextrin, lactose, microcrystalline cellulose, pregelatinized starch, xylitol, mannitol, sorbitol, erythritol, sucrose, glucose, fructose, trehalose, and maltose.

In a further preferred embodiment, the said auxiliary component B) further comprises the following components:
a disintegrating agent: being one or more selected from the group consisting of low-substituted hydroxybenzoate cellulose, sodium carboxymethyl starch, crosslinked polyvinylpyrrolidone, crosslinked sodium carboxymethyl cellulose, crosslinked sodium carboxymethyl starch;
a masking agent: being selected from the group consisting of cyclodextrin and derivatives thereof, polyethylene glycol, polyvinylpyrrolidone, methacrylic acid polymer;
a binding agent: being selected from the group consisting of an ethanol solution, water, a polyvinylpyrrolidone solution, and a starch slurry;
an effervescent agent: being selected from the group consisting of citric acid, tartaric acid, boric acid, fumaric acid, sodium hydrogen carbonate, and sodium carbonate;
a flavoring agent: being selected from the group consisting of peppermint essence, lemon essence, sodium cyclamate, Aspartame, and stevioside;
a glidant: being selected from micro-powder silica gel;
a lubricant: being selected from the group consisting of talc powder, magnesium stearate, and polyethylene glycol;
the amount of each of the auxiliary components in B) may be as follows: a filling agent 10-95, a disintegrant 0-50, a masking agent 0-50, a binding agent 0-10, an effervescent agent 0-60, a flavoring agent 0-20, a glidant 0-15, and a lubricant 0-30, in portions of weight in the auxiliary components B).

A fourth object of the present invention is to provide a process for preparing an oral disintegrating tablet of total secondary ginsenosides, which is achieved as follows:

A process for preparing an oral disintegrating tablet of total secondary ginsenosides, comprising the following steps:
(1) Preparation of an extract liquid of total ginsenosides: extracting a plant of *Panax* genus with water or an organic solvent, then concentrating the resulting extract liquid;
(2) Preparation of hydrolyzate liquid: hydrolyzing the above concentrated extract liquid in the presence of an inorganic or organic acid as catalyst;
(3) Absorption with resin: passing the hydrolyzate liquid through a macroporous resin for absorption on column;
(4) Removal of impurities: eluting the absorption column that has absorbed the hydrolyzate liquid with water, an alkaline aqueous solution, and ethanol having a concentration below 35%, to remove the impurities;
(5) Elution, concentration, drying: after the removal of impurities, eluting the absorption column with an ethanol solution having a concentration of above 35%, collecting the eluent eluted with ethanol at a concentration of above 35%, concentrating the resulting eluent to obtain a liquid extract, and drying under vacuum to obtain a pharmaceutical composition of total secondary ginsenosides as the component A);
(6) Mixing homogeneously the component A of the pharmaceutical composition of total secondary ginsenosides as obtained in the step (5) with the auxiliary components B), drying, pulverizing, and tableting in a convention manner to obtain the tablet.

A fifth object of the present invention is to provide uses of a pharmaceutical composition of total secondary ginsenosides in the manufacture of a medicament for treatment of any of the following diseases:

Use in the manufacture of a medicament for treatment of angina pectoris of coronary heart disease;

Use in the manufacture of a medicament for treatment of myocardial ischemia;

Use in the manufacture of a medicament for treatment of hemorrhagic shock; and

Use in the manufacture of a medicament for treatment of heart failure.

The present invention is further illustrated by the examples as follows, but these examples are not intended to limit the protection scope of the present invention.

EXAMPLES

Example 1

10 kg of fibrous ginseng root was extracted with 70% ethanol under refluxing condition for 3 times, each with 5-fold amount of solvent for 3 hours. All the extract liquids were pooled and concentrated under reduced pressure. Into the concentrated liquid was added an equal volume of 99% glacial acetic acid, and the hydrolysis was performed at 97-99° C. for 3 hours. Into the hydrolyzate liquid was added an equal volume of water, and then passed through a D101 type macroporous resin column. After completely loading, the column was eluted with water until almost colorless, then eluted with 0.5% sodium hydroxide, eluted with water until neutral, then eluted with 20% ethanol, and finally eluted with 70% ethanol. The eluent eluted with 70% ethanol was collected, concentrated under reduced pressure to obtain an extract liquid, dried under vacuum at 70° C. to obtain 0.56 kg of an extract of total secondary ginsenosides. The contents of various active components were measured by high pressure liquid chromatography to be: 20-(S)-Rg3 9.0%, 20-(R)-Rg3 9.0%, 20-(S)-Rg2 5.1%, 20-(R)-Rg2 5.1%, 20-(S)-Rh1 3.8%, and 20-(R)-Rh1 3.8%. By using ginsenoside 20-(R)-Rg3 as the reference, the content of total secondary ginsenosides was measured by colorimetry as 62%. The residual was plant pigments and daucosterols.

For 50 g of the obtained pharmaceutical composition of total secondary ginsenosides, microcrystalline cellulose and mannitol were pulverized separately, screened and stored for use; 15 g of methacrylate polymer Eudragit E100 was dissolved in an appropriate amount of an ethanol solution, the total secondary ginsenosides were added slowly with stirring, then continued stirring until the total secondary ginsenosides were dispersed homogenously, dried under reduced pressure, pulverized, and then screened. 10 g of crosslinked polyvinylpyrrolidone, 70 g of microcrystalline cellulose, 190 g of mannitol, 2 g of aspartame, 17.5 g of micro-powder silica gel, and 1.5 g of magnesium stearate were added, mixed homogenously, measured to determine their contents, calculated to determine the weight of the tablet, and then tableted to obtain oral disintegrating tablets of total secondary ginsenosides.

Example 2

10 kg of decocting tablets (or crude pieces) of ginseng was extracted with 70% ethanol under refluxing condition for 3 times, each with 6 volume of solvent for 3 hours. All the extract liquids were pooled and concentrated under reduced pressure. Into the concentrated liquid was added equal volume of 0.1% hydrochloric acid, and then the mixture was hydrolyzed at 80-83° C. for 8 hours. Into the hydrolyzate liquid was added an equal volume of water, and then the mixture was passed through a D2 type macroporous resin column. After completely loading, the column was eluted with water until almost colorless, then eluted with 5.0% potassium hydroxide, followed by water until neutral, eluted with 15% ethanol, and finally eluted with 60% ethanol. The eluent eluted with 60% ethanol was collected, concentrated under reduced pressure to obtain an extract liquid, dried under vacuum at 70° C., resulting in 0.35 kg of an extract of total secondary ginsenosides. The obtained extract of total secondary ginsenosides was separated by chromatography using a silica gel column (200-300 mesh, 10 kg), the mobile phase being dichloromethane-methanol gradient eluent, and the eluants were detected by silica gel thin layer chromatography. The fractions containing ginsenoside Rg3, ginsenoside Rg2 and ginsenoside Rh1 were pooled, evaporated to remove dichloromethane-methanol, resulting in an extract of total secondary ginsenosides with a white-like color.

The contents of the various active ingredients therein were measured by high pressure liquid chromatography as follows: 20-(S)-Rg3 25.0%, 20-(R)-Rg3 25.0%, 20-(S)-Rg2 4.2%, 20-(R)-Rg2 4.2%, 20-(S)-Rh1 4.7%, and 20-(R)-Rh1 4.7%. By using ginsenoside 20-(R)-Rg3 as the reference, the content of total secondary ginsenosides in the extract was measured by colorimetry as 98.5%. The residual was steroids and glycosides thereof.

10 g of the obtained extract of total secondary ginsenosides and 5 ml of Tween-80 were dissolved in 1500 ml water for injection, then an appropriate amount of water for injection was added until the volume reached 2000 ml, then the resultant solution was filtered, aliquoted, and sterilized to obtain an injection solution of total secondary ginsenosides.

Example 3

10 kg of decocting tablet of notoginseng was extracted with 70% ethanol under a refluxing condition for 3 times, each with 5-fold amount of solvent for three hours. All the extract liquids were pooled and concentrated under reduced pressure. Into the concentrated liquid was added an equal volume of 99% glacial acetic acid, then the mixture was hydrolyzed at 87-89° C. for 5 hours. Into the hydrolyzate liquid was added an equal volume of water, and then the mixture was passed through a DM2 type macroporous resin column. After completely loading, the column was eluted with water until almost colorless, then eluted with 3.5% sodium hydroxide, followed by water until neutral, then eluted with 25% ethanol, and finally eluted with 80% ethanol. The 80% ethanol eluant was collected, concentrated under reduced pressure to obtain an extract liquid, dried under vacuum at 70° C., resulting in 0.38 kg of an extract of total secondary ginsenosides. The contents of various active ingredients therein were measured by high pressure liquid chromatography as follows: 20-(S)-Rg3 5.7%, 20-(R)-Rg3 5.7%, 20-(S)-Rg2 9.3%, 20-(R)-Rg2 9.3%, 20-(S)-Rh1 8.2%, and 20-(R)-Rh1 8.2%. By using ginsenoside 20-(R)-Rg3 as the reference, the content of total secondary ginsenosides in the extract was measured by colorimetry as 65%. The residual was plant pigments, β-sitosterol and daucosterols.

50 g of the obtained pharmaceutical composition of total secondary ginsenosides, 30 g of starch, 55 g of citric acid, 55 g of tartaric acid, 40 g of sodium hydrogen carbonate, 5 g of peppermint essence, 15 g of sodium cyclamate, 45 g of micropowder silica gel, and 5 g of talc powder were weighed and mixed homogenously, measured to determine their contents, calculated to determine the tablet weight, and then tableted, resulting in tablets of total secondary ginsenosides.

Example 4

10 kg of ginseng stems and leaves was extracted with 70% ethanol under refluxing condition for 3 times, each with 5-fold amount of solvent for three hours. All the extract liquids were pooled and concentrated under reduced pressure. Into the concentrated liquid was added an equal volume of glacial acetic acid, and then the mixture was hydrolyzed at 90-93° C. for 7 hours. The hydrolyzate liquid was concentrated under reduced pressure to obtain an extract liquid, dried under vacuum at 70° C. to obtain 0.71 kg of an extract of total secondary ginsenosides. The contents of various active components were measured by high pressure liquid chromatography as follows: 20-(S)-Rg3 3.5%, 20-(R)-Rg3 3.5%, 20-(S)-Rg2 0.5%, 20-(R)-Rg2 0.5%, 20-(S)-Rh1 0.4%, and 20-(R)-Rh1 0.4%. By using ginsenoside 20-(R)-Rg3 as the reference, the content of total secondary ginsenosides in the extract was measured by colormetry as 21%. The residual was ginsing polysaccharides, plant pigments, flavones and glcosides thereof, β-sitosterol and daucosterols.

100 g of the obtained extract of total secondary ginsenosides, 50 ml of Tween-80, 1 g of ethyl hydroxybenzoate, 1 g of propyl hydroxybenzoate, 5 g of sodium saccharin were weighed and dissolved in 8000 ml water, then an appropriate amount of water was added to reach a volume of 10000 ml, and the resultant solution was filtered, aliquoted to obtain an oral liquid of total secondary ginsenosides.

Example 5

10 kg of decocting tablets of American ginseng was extracted with 50% ethanol under refluxing condition for 3 times, each with 7-fold amount of solvent for 2.5 hours. All extract liquids were pooled and concentrated under reduced pressure. Into the concentrated liquid was added an equal amount of glacial acetic acid, and then the mixture was hydrolyzed at 97-99° C. for 5 hours. Into the hydrolyzate liquid was added an equal volume of water, and then the mixture was passed through a DS2 type macroporous resin column. After completely loading, the column was eluted with water until almost colorless, then eluted with 0.8% potassium hydroxide, eluted with water until neutral, eluted with 20% ethanol, and finally eluted with 80% ethanol. The eluant eluted with 80% ethanol was collected, concentrated under reduced pressure to obtain an extract liquid, dried under vacuum at 70° C. to obtain 0.35 kg of an extract of total secondary ginsenosides. The contents of various active components were measured by high pressure liquid chromatography to be as follows: 20-(S)-Rg3 11.0%, 20-(R)-Rg3 11.0%, 20-(S)-Rg2 0.9%, 20-(R)-Rg2 0.9%, 20-(S)-Rh1 1.2%, and 20-(R)-Rh1 1.2%. By using ginsenoside 20-(R)-Rg3 as the reference, the content of total secondary ginsenosides was measured by colorimetry as 57%. The residue was plant pigments, β-sitosterol and daucosterols.

50 g of the obtained extract of total secondary ginsenosides was weighed, into which were added 1500 g of starch, 100 g of sodium cyclamate, 250 g of microcrystalline cellulose, and 100 g of carboxymethyl cellulose, and mixed homogeneously, granulated, dried, and aliquoted, resulting in granules of total secondary ginsenosides.

Example 6

10 kg of notoginseng stems and leaves was extracted with 60% ethanol under refluxing condition for 3 times, each with 5-fold amount of solvent for 4 hours. All extract liquids were pooled and concentrated under reduced pressure. Into the concentrated liquid was added an equal weight of 0.5% sulfuric acid, then the mixture was hydrolyzed at 50-53° C. for 1 hour. Into the hydrolyzate liquid was added an equal volume of water, and then the mixture was passed through a XAD-1 type macroporous resin column. After completely loading, the column was eluted with water until almost colorless, then eluted with 0.5% potassium hydroxide, eluted with water until neutral, then eluted with 15% ethanol, and finally eluted with 65% ethanol. The eluants by 65% ethanol were collected, concentrated under reduced pressure to obtain an extract liquid, dried under vacuum at 70° C. to obtain 0.45 kg of an extract of total secondary ginsenosides. The contents of various active components were measured by high pressure liquid chromatography to be: 20-(S)-Rg3 15.5%, 20-(R)-Rg3 15.5%, 20-(S)-Rg2 1.1%, 20-(R)-Rg2 1.1%, 20-(S)-Rh1 1.2%, and 20-(R)-Rh1 1.2%. By using ginsenoside 20-(R)-Rg3 as the reference, the content of total secondary ginsenosides in the extract was measured by colorimetry as 70%. The residual was plant pigments, sterols and daucosterols.

50 g of the obtained extract of total secondary ginsenosides and 450 g of polyethylene glycol 6000 were weighed. The polyethylene glycol 6000 was heated to about 100° C., then the extract of total secondary ginsenosides was added, kept being heated for dissolving and mixed homogenously. The mixture solution was dropped into liquid paraffin as cooling liquid, cooled to form pills, and dried to obtain drop pills of total secondary ginsenosides.

Example 7

10 kg of American ginseng stems and leaves was extracted with 70% ethanol under refluxing condition for 3 times, each with 5-fold amount of solvent for 3 hours. All the extract liquids were pooled and concentrated under reduced pressure. Into the concentrated liquid was added an equal amount of propionic acid, and the mixture was hydrolyzed at 108-110° C. for 7 hours. Into the hydrolyzate liquid was added an equal volume of water, and then the mixture was passed through a HP-30 type macroporous resin column. After completely loading, the column was eluted with water until almost colorless, then eluted with 5% potassium carbonate, eluted with water until neutral, then eluted with 35% ethanol, and finally eluted with 95% ethanol. The eluant by 95% ethanol was collected, concentrated under reduced pressure to obtain an extract liquid, dried under vacuum at 70° C. to obtain 0.23 kg of an extract of total secondary ginsenosides. The contents of various effective components in the resulting extract were measured by high pressure liquid chromatography to be: 20-(S)-Rg3 10.5%, 20-(R)-Rg3 10.5%, 20-(S)-Rg2 1.1%, 20-(R)-Rg2 1.1%, 20-(S)-Rh1 1.0%, and 20-(R)-Rh1 1.0%. By using ginsenoside 20-(R)-Rg3 as the reference, the content of total secondary ginsenosides in the extract was measured by colorimetry as 52%. The residual was plant pigments, flavones, β-sitosterol and daucosterols.

50 g of the obtained extract of total secondary ginsenosides was weighed, into which was added 100 g of starch and 5 g of magnesium stearate, then the mixture was mixed homogeneously, granulated, dried, loaded into 1000 capsules to obtain capsules of total secondary ginsenosides.

Example 8

10 kg of decocting tablets of sun-dried ginseng was extracted with 70% ethanol under refluxing condition for 3 times, each with 5-fold amount of solvent for 3 hours. All the extract liquids were combined and concentrated under reduced pressure. Into the concentrated liquid was added an equal amount of propionic acid, and then the mixture was hydrolyzed at 97-99° C. for 9 hours. Into the hydrolyzate liquid was added an equal volume of water, and then the mixture was passed through a XAD-5 type macroporous resin column. After completely loading, the column was eluted with water until almost colorless, then eluted with 0.1% sodium hydroxide, eluted with water until neutral, then eluted with 35% ethanol, and finally eluted with 50% ethanol. The eluant by 50% ethanol was collected, concentrated under reduced pressure to obtain an extract liquid, dried under vacuum at 70° C. to obtain 0.18 kg of an extract of total secondary ginsenosides. The contents of various active components in the extract were measured by high pressure liquid chromatography to be: 20-(S)-Rg3 8.5%, 20-(R)-Rg3 8.5%, 20-(S)-Rg2 2.0%, 20-(R)-Rg2 2.0%, 20-(S)-Rh1 1.6%, and 20-(R)-Rh1 1.6%. By using ginsenoside 20-(R)-Rg3 as the reference, the content of total secondary ginsenosides in the extract was measured by colorimetry as 58%. The residual was plant pigments and daucosterols.

Example 9

10 kg of decocting tablets of red ginseng was extracted with 70% ethanol under refluxing condition for 3 times, each with 5-fold amount of solvent for 3 hours. All the extract liquids were combined and concentrated under reduced pressure. Into the concentrated liquid was added an equal amount of glacial acetic acid, and then the mixture was hydrolyzed at 97-99° C. for 5 hours. Into the hydrolyzate liquid was added an equal volume of water, and then the mixture was passed through a HP-10 type macroporous resin column. After completely loading, the column was eluted with water until almost colorless, then eluted with 0.3% sodium hydroxide, eluted with water until neutral, then eluted with 20% ethanol, and finally eluted with 70% ethanol. The eluant by 70% ethanol was collected, concentrated under reduced pressure to obtain an extract liquid, and dried under vacuum at 70° C. to obtain 0.25 kg of an extract of total secondary ginsenosides. The contents of various effective components in the extract were measured by high pressure liquid chromatography to be: 20-(S)-Rg3 8.8%, 20-(R)-Rg3 8.8%, 20-(S)-Rg2 2.2%, 20-(R)-Rg2 2.2%, 20-(S)-Rh1 1.9%, and 20-(R)-Rh1 1.9%. By using ginsenoside 20-(R)-Rg3 as the reference, the content of total secondary ginsenosides in the extract was measured by colorimetry as 55%. The residual was plant pigments, β-sitosterol and daucosterols.

Test Example 1

Effects on Myocardial Ischemia Induced by Coronary Artery Ligation in Anesthetized Dogs Test dogs were divided into the following 8 groups, 6 dogs per group: (1) blank control group, 3 ml/kg physiological saline; (2) 5 mg/kg Diltiazem group; (3) 200 mg/kg "Di'ao Xinxuekang" group; (4) 200 mg/kg ginseng root total ginsenosides (briefly referred as root total ginsenosides) group; (5) 200 mg/kg ginseng stem/leave total ginsenosides (briefly referred as stem/leave total ginsenosides) group; (6) 25 mg/kg total secondary ginsenosides group; (7) 50 mg/kg total secondary ginsenosides group; and (8) 100 mg/kg total secondary ginsenosides group. All test drugs were formulated with distilled water to have the same volume (3 ml/kg), and were administered through duodenum.

Animals each was anesthetized with sodium pentobarbital (30 mg/kg), operated to form pericardium bed; left circumflex artery was separated, an electromagnetic flow meter probe was placed therein to measure cardiac coronary blood flow (CCBF); middle section of anterior descending coronary artery was separated, braided for ligation to create an experimental acute myocardial ischemia model; a multipoint fixed epicardial lead was sutured and connected with a multichannel electrophysiolograph to record epicardial electrogram. Coronary artery was ligated for 15 minutes, and recorded as control value before administration of drug, test drug or physiological saline was administered via duodenum, 30 mapping point epicardial electrograms were recorded at 15, 30, 45, 60, 90, 120, 180 minutes after the administration of drug, and the degree of myocardial ischemia (Σ-ST, total increase of mv number in S-T section) and the range of myocardial ischemia (N-ST, total increase of point numberin S-T section) were calculated. Blood samples were taken at orifice of coronary sinus vein by cannulation via external jugular vein before ischemia, at 15 minutes after ischemia (before administration of drug), and at 0, 30, 60, 90, 120, 180 minutes after administration of drug, the contents of oxygen in the coronary venous blood were measured by oxyhemograph; cannulation was made to common carotid artery, where the contents of blood in the arterial blood were measured, which together with coronary blood flow were used to calculate myocardial oxygen consumption (MOC). Blood samples were taken at the abovementioned time points to measure the levels of serum creatine kinase (CK) and lactic acid dehydrogenase (LDH); and the levels of blood plasma endothelin (ET), thromboxane $B_2$ ($TXB_2$) and 6-keto-prostaglandin $F_{1a}$ (6-Keto-$PGF_{1a}$) were measured by an automatic γ-counter radioimmunologically.

Recording was completed at 180 minutes after administration of drug, heart was taken out immediately, cardiac ventricle was cross-sectioned parallel to coronary sulcus under heart ligature to form 5 slices, which were placed in N-BT staining solution and stained at room temperature for 15 minutes. Infarction zone (N-BT non-staining zone) and non-infarction zone (N-BT staining zone) at both sides of each slice of cardiac muscle were measured by using a multimedia color pathologic image analysis system to calculate the area of each slice of cardiac muscle, the total area of the cardiac ventricle and the total area of the infarction zones. The percentages of infarction zones based on the cardiac ventricle and on the whole heart were calculated.

The test results were statistically analyzed, and t-test was used to determine the significance.

The results were shown in Table 1, wherein the degree of myocardial ischemia ($\Sigma$-ST) in the physiological saline control group did not change significantly; the root total ginsenosides and the stem/leave total ginsenosides at dosage of 200 mg/kg could significantly inhibit myocardial ischemia and reduce $\Sigma$-ST; all three dosage groups of the total secondary ginsenosides exhibited reduced degree of myocardial ischemia, being significantly at 90-180 minutes, and the total secondary ginsenosides at dosage of 50-100 mg/kg reduced $\Sigma$-ST at approximately the same degree as, or a slightly higher degree than that achieved by the root total ginsenosides and the stem/leave total ginsenosides, all higher than 50%.

The above results indicated that the total secondary ginsenosides had stronger effectiveness than the root total ginsenosides and the stem/leave total ginsenosides.

Effects on the Range of Myocardial Ischemia (N-ST) in Dogs

The results were shown in Table 2, indicating that after administration of physiological saline, the range of myocardial ischemia (N-ST) in the control group did not change significantly. The groups with various total ginsenosides obtained from different parts of ginseng did not exhibit any significant change, while in the groups of the total secondary ginsenosides, significant effects were at 90-180 minutes after the administration at the dosage of 100 mg/kg, and the differences were significant (P<0.05) in comparison with the results got before administration and with that in the control group.

The above results indicated that the total secondary ginsenosides exhibited significant improvement effects on experimental acute myocardial ischemia in dogs, could significantly reduce the degree of myocardial ischemia ($\Sigma$-ST), and were more effective than the total ginsenosides from the various parts of ginseng.

Test Example 2

Effects on the Range of Acute Myocardial Infarction in Dogs

Measured by N-BT Staining Method

The results were shown in Table 3, the myocardial infarction zones in the animals of the physiological saline control group were 7.41±1.67% and 16.75±3.40% based on heart and cardiac ventricle respectively; the three dosage groups of total secondary ginsenosides could reduce the area of myocardial infarction zone in animals, and the area of myocardial infarction zone was 3.20±1.85% and 7.85±4.74% based on heart and cardiac ventricle respectively, i.e., the area was decreased by 56.81% and 53.13%, respectively, which were very significantly different from the physiological saline control group (both P<0.001). The total ginsenosides from root, stem/leave of ginseng also could significantly reduce the area of myocardial infarction, but were less effective than the total secondary ginsenosides, with no significant difference.

The results indicated that the total secondary ginsenosides at a dosage lower than that of the total ginsenosides of root and stem/leave of ginseng could reach or even slightly exceed the effectiveness and effects of the later two.

Test Example 3

Effects on Coronary Blood Flow in Experimental Myocardial Ischemia Dogs

The results were shown in Table 4, indicating that after the coronary artery of anesthetized dog was ligated to form myocardial ischemia, the coronary blood flow exhibited a compensatory increase for a short time period at an amplitude of about 10%. The root total ginsenosides and the stem/leave total ginsenosides could both increase the coronary blood flow, and the total secondary ginsenosides could significantly increase the coronary blood flow after administration, wherein the three dosage groups all exhibited significant increase in coronary blood flow at 15-180 minutes after administration, and the increase of coronary blood flow during 60 min-120 min was the most significant. In comparison with that before administration of drug (P<0.01) and that in the physiological saline group (P<0.001), the difference was significant, and their effectiveness was equivalent to that of the root total ginsenosides and stem/leave total ginsenosides.

The results showed that the total secondary ginsenosides at a dosage lower than that of the total ginsenosides of root and stem/leave of ginseng could reach the same effectiveness and effects as the later two.

TABLE 1

Effects of the drugs on the degree of acute myocardial ischemia ($\Sigma$-ST) in each group of dogs (epicardial electrogram mapping) ($\overline{X}$ ± SD)

| Group | Dosage mg/kg | Before administration of drug Change rate (100%) | After administration of drug (min) | | | |
|---|---|---|---|---|---|---|
| | | | 15 | 30 | 45 | 60 |
| Physiological saline (n = 6) | 3 ml | 219.33 ± 68.31 (100%) | 197.33 ± 41.74 86.08 ± 35.65 | 223.83 ± 46.18 100.38 ± 41.16 | 258.17 ± 64.44 115.10 ± 58.03 | 264.33 ± 63.11 116.33 ± 52.02 |
| Diltiazem (n = 6) | 5 | 291.00 ± 40.39 (100%) | 182.00 ± 70.40## 61.01 ± 20.89** | 149.83 ± 41.36## 48.75 ± 9.99** | 126.00 ± 47.35## 42.43 ± 8.97** | 148.67 ± 71.87## 47.78 ± 10.82** |
| Di'ao | 200 | 322.33 ± 111.75 | 208.67 ± 73.44## | 222.00 ± 53.28# | 215.33 ± 105.47# | 201.33 ± 81.24# |

TABLE 1-continued

Effects of the drugs on the degree of acute myocardial ischemia (Σ-ST) in each group of dogs (epicardial electrogram mapping) ($\overline{X} \pm SD$)

| Group | Dosage mg/kg | | | | | |
|---|---|---|---|---|---|---|
| Xinxuekang (n = 6) | | (100%) | 65.05 ± 10.77 | 72.17 ± 17.79 | 68.22 ± 28.92 | 66.64 ± 33.55 |
| Root total ginsenosides (n = 6) | 200 | 359.67 ± 97.65 (100%) | 279.50 ± 100.03## 76.39 ± 7.41 | 226.00 ± 65.01## 63.08 ± 7.31 | 226.50 ± 79.16# 63.59 ± 17.70 | 185.00 ± 71.14## 50.75 ± 7.30* |
| Stem/leave total ginsenosides (n = 6) | 200 | 339.17 ± 86.98 (100%) | 218.83 ± 43.84# 67.24 ± 16.45 | 205.50 ± 45.01# 63.54 ± 16.70 | 237.00 ± 72.37 75.59 ± 33.35 | 216.33 ± 63.59# 66.21 ± 20.64 |
| Total secondary ginsenosides (n = 6) | 25 | 303.83 ± 93.38 (100%) | 250.17 ± 67.29## 83.25 ± 5.61 | 253.83 ± 98.13 83.74 ± 15.13 | 295.67 ± 150.22 95.20 ± 21.10 | 303.17 ± 127.18 99.83 ± 20.84 |
| Total secondary ginsenosides (n = 6) | 50 | 339.17 ± 161.96 (100%) | 259.33 ± 134.31# 77.37 ± 18.84 | 250.00 ± 83.31 77.79 ± 18.50 | 228.17 ± 51.09 73.40 ± 20.49 | 226.50 ± 55.82 74.18 ± 28.28 |
| Total secondary ginsenosides (n = 6) | 100 | 375.67 ± 127.18 (100%) | 299.67 ± 103.55# 80.34 ± 10.15 | 254.33 ± 47.55# 74.35 ± 31.02 | 244.33 ± 52.65# 69.04 ± 18.25 | 225.67 ± 92.25# 60.78 ± 20.51* |

| Group | Dosage mg/kg | Before administration of drug Change rate (100%) | After administration of drug (min) | | |
|---|---|---|---|---|---|
| | | | 90 | 120 | 180 |
| Physiological saline (n = 6) | 3 ml | 219.33 ± 68.31 (100%) | 306.17 ± 74.08 141.84 ± 53.86 | 327.17 ± 128.01 148.33 ± 63.70 | 301.50 ± 122.58 139.96 ± 56.56 |
| Diltiazem (n = 6) | 5 | 291.00 ± 40.39 (100%) | 140.17 ± 63.46## 54.98 ± 18.57** | 139.00 ± 69.20## 52.21 ± 19.91** | 117.17 ± 54.27## 45.99 ± 18.90** |
| Di'ao Xinxuekang (n = 6) | 200 | 322.33 ± 111.75 (100%) | 182.83 ± 88.06# 61.13 ± 36.29* | 180.00 ± 95.61# 59.74 ± 36.37* | 140.83 ± 71.17# 48.47 ± 34.06** |
| Root total ginsenosides (n = 6) | 200 | 359.67 ± 97.65 (100%) | 165.17 ± 66.56## 45.49 ± 11.59** | 159.83 ± 67.93## 43.43 ± 9.22** | 145.83 ± 48.86## 41.03 ± 8.40** |
| Stem/leave total ginsenosides (n = 6) | 200 | 339.17 ± 86.98 (100%) | 223.50 ± 64.05# 69.25 ± 26.66* | 214.67 ± 74.59# 65.94 ± 26.94* | 179.00 ± 75.07## 53.59 ± 21.16** |
| Total secondary ginsenosides (n = 6) | 25 | 303.83 ± 93.38 (100%) | 322.50 ± 147.34 103.87 ± 25.75 | 267.83 ± 119.66 86.28 ± 15.00* | 223.33 ± 94.59## 72.52 ± 16.36* |
| Total secondary ginsenosides (n = 6) | 50 | 339.17 ± 161.96 (100%) | 211.67 ± 88.49 65.63 ± 22.93* | 183.83 ± 55.49# 53.50 ± 21.37* | 161.17 ± 94.28# 45.77 ± 20.75* |
| Total secondary ginsenosides (n = 6) | 100 | 375.67 ± 127.18 (100%) | 203.00 ± 104.24## 52.77 ± 13.68** | 190.67 ± 95.41## 48.76 ± 22.34** | 148.33 ± 79.84## 40.32 ± 14.27** |

Note:
being comparing with that the results before the administration of drug:
P < 0.05,
P < 0.01; being compared with the control group:
*P < 0.05,
**P < 0.01

TABLE 2

Effects of the drugs on the degree of acute myocardial ischemia (N-ST) in each group of dogs (epicardial electrogram mapping) ($\overline{X} \pm SD$)

| Group | Dosage mg/kg | Before administration of drug Change rate (100%) | After administration of drug (min) | | | | | | |
|---|---|---|---|---|---|---|---|---|---|
| | | | 15 | 30 | 45 | 60 | 90 | 120 | 180 |
| Physiological saline (n = 6) | 3 ml | 27.83 ± 3.06 (100%) | 27.33 ± 3.27 97.93 ± 1.89 | 27.50 ± 3.73 100.13 ± 4.41 | 26.50 ± 4.37 95.61 ± 8.04 | 25.67 ± 4.46 92.77 ± 10.83 | 26.67 ± 3.88 95.71 ± 4.09 | 27.00 ± 4.10 96.35 ± 5.19 | 26.17 ± 3.66 92.92 ± 2.75 |
| Diltiazem (n = 6) | 5 | 28.67 ± 0.82 (100%) | 24.83 ± 2.04# 89.60 ± 8.40* | 25.33 ± 4.08 89.53 ± 15.49 | 23.17 ± 5.91 86.82 ± 14.83 | 23.50 ± 4.85 87.48 ± 15.08 | 21.50 ± 5.86# 81.41 ± 14.31* | 20.00 ± 6.00# 77.22 ± 16.49* | 20.67 ± 5.99# 75.89 ± 19.59* |

TABLE 2-continued

Effects of the drugs on the degree of acute myocardial ischemia (N-ST) in each group of dogs (epicardial electrogram mapping) ($\overline{X} \pm SD$)

| Group | Dosage mg/kg | Before administration of drug Change rate (100%) | After administration of drug (min) | | | | | | |
|---|---|---|---|---|---|---|---|---|---|
| | | | 15 | 30 | 45 | 60 | 90 | 120 | 180 |
| Di'ao Xinxuekang (n = 6) | 200 | 29.67 ± 0.82 (100%) | 26.50 ± 4.93 89.01 ± 14.88 | 26.83 ± 4.58 90.16 ± 13.62 | 26.17 ± 5.19 87.90 ± 15.90 | 26.17 ± 5.60 87.94 ± 17.46 | 25.50 ± 4.55 85.75 ± 13.94 | 24.00 ± 5.02 80.71 ± 15.77 | 22.50 ± 5.01# 77.21 ± 16.52* |
| Root total ginsenosides (n = 6) | 200 | 29.17 ± 1.60 (100%) | 28.50 ± 1.97 97.67 ± 2.78 | 26.83 ± 3.71 91.69 ± 9.03 | 26.67 ± 3.72 91.13 ± 9.26 | 25.33 ± 4.13# 86.58 ± 11.06 | 24.83 ± 4.75 85.19 ± 15.63 | 24.33 ± 5.16 83.51 ± 17.25 | 24.00 ± 6.03 82.40 ± 20.65 |
| Stem/leave total ginsenosides (n = 6) | 200 | 29.83 ± 0.41 (100%) | 29.50 ± 0.84 98.89 ± 2.72 | 29.50 ± 0.84 98.91 ± 3.47 | 29.33 ± 0.82 98.35 ± 3.53 | 29.33 ± 0.82 98.35 ± 3.53 | 28.50 ± 1.05 95.56 ± 4.04 | 28.33 ± 1.97 95.00 ± 6.91 | 27.17 ± 3.66 91.11 ± 12.59 |
| Total secondary ginsenosides (n = 6) | 25 | 29.17 ± 1.17 (100%) | 28.83 ± 1.47 98.83 ± 1.82 | 28.50 ± 1.38 97.72 ± 2.76 | 28.67 ± 1.03 98.31 ± 1.85 | 29.17 ± 0.75 100.06 ± 2.23 | 28.83 ± 0.41 98.95 ± 2.84 | 29.00 ± 0.63 99.51 ± 2.63 | 28.67 ± 1.03 98.31 ± 1.85 |
| Total secondary ginsenosides (n = 6) | 50 | 29.67 ± 0.52 (100%) | 29.00 ± 1.26 97.76 ± 4.04 | 29.17 ± 0.98 98.31 ± 2.80 | 29.33 ± 0.82 98.87 ± 1.75 | 29.33 ± 0.52 98.89 ± 1.72 | 29.50 ± 0.55 99.46 ± 2.55 | 29.00 ± 0.89 97.80 ± 4.07 | 26.33 ± 3.44 88.81 ± 11.95 |
| Total secondary ginsenosides (n = 6) | 100 | 29.67 ± 0.52 (100%) | 29.50 ± 0.55 99.44 ± 1.36 | 28.67 ± 0.52 98.00 ± 3.00 | 27.67 ± 0.52 97.00 ± 5.56 | 26.50 ± 0.55 89.44 ± 7.36 | 25.17 ± 0.75# 85.33 ± 2.79* | 24.33 ± 3.14# 80.76 ± 10.89* | 22.00 ± 4.47# 78.09 ± 15.44* |

Note:
being compared with the results before the administration of drug:
P < 0.05
P < 0.01
P < 0.001; being compared with the control group:
*P < 0.05,
**P < 0.01

TABLE 3

Effects of the drugs on the range of acute myocardial ischemia in each group of dogs ($\overline{X} \pm SD$)

| Group | Dosage mg/kg | Animals n | Heart area (mm$^2$) | Cardiac ventricle area (mm$^2$) | Infarction zone area (mm$^2$) | Infraction zone/heart | Infraction zone/cardiac ventricle |
|---|---|---|---|---|---|---|---|
| Physiological saline | 3 ml | 6 | 11857.4 ± 1306.8 | 5193.6 ± 186.1 | 865.50 ± 151.0 | 7.41 ± 1.67 | 16.75 ± 3.40 |
| Diltiazem | 5 | 6 | 12221.5 ± 1980.9 | 5070.3 ± 405.8 | 266.25 ± 63.4*** | 2.27 ± 0.83*** | 5.36 ± 1.70*** |
| Di'ao Xinxuekang | 200 | 6 | 12150.2 ± 1694.3 | 5179.2 ± 574.4 | 410.52 ± 163.6** | 3.43 ± 1.39** | 8.01 ± 3.04** |
| Root total ginsenosides | 200 | 6 | 11872.7 ± 1532.4 | 5224.4 ± 529.2 | 438.42 ± 112.2** | 3.75 ± 1.12** | 8.39 ± 2.11** |
| Stem/leave total ginsenosides | 200 | 6 | 12146.4 ± 1227.6 | 5177.1 ± 227.2 | 417.17 ± 125.5** | 3.48 ± 1.16** | 8.07 ± 2.40** |
| Total secondary ginsenosides | 25 | 6 | 13694.6 ± 3738.3 | 5374.8 ± 891.4 | 374.92 ± 132.8** | 2.76 ± 0.87* | 6.90 ± 2.05** |
| Total secondary ginsenosides | 50 | 6 | 11995.9 ± 1681.4 | 5182.7 ± 683.5 | 407.17 ± 170.0** | 3.44 ± 1.38** | 7.87 ± 2.85** |
| Total secondary ginsenosides | 100 | 6 | 12403.5 ± 1994.1 | 4974.3 ± 585.3 | 402.50 ± 277.2** | 3.20 ± 1.85** | 7.85 ± 4.74** |

Note:
being compared with the control group:
*P < 0.05,
**P < 0.01,
***P < 0.001

TABLE 4

Effects of the drugs on the coronary blood flow (ml/100 g · min$^{-1}$) in each group of dogs ($\overline{X} \pm SD$)

| Group | Dosage mg/kg | Before ischemia (normal value) | After ischemia (before administration of drug) Change rate (100%) | After administration of drug (min) 30 | 60 | 90 |
|---|---|---|---|---|---|---|
| Physiological saline (n = 6) | 3 ml | 80.55 ± 40.05 | 89.95 ± 44.44<br>112.35 ± 1.81 | 89.11 ± 42.82<br>100.65 ± 8.14 | 89.91 ± 43.71<br>98.94 ± 6.98 | 85.94 ± 42.76<br>96.29 ± 8.55 |
| Diltiazem (n = 6) | 5 | 92.07 ± 46.98 | 101.82 ± 54.71#<br>110.34 ± 4.17 | 110.36 ± 58.20##<br>108.70 ± 3.32* | 119.11 ± 61.62###<br>117.06 ± 5.17*** | 122.97 ± 64.44##<br>120.06 ± 7.27*** |
| Di'ao Xinxuekang (n = 6) | 200 | 96.17 ± 53.08 | 101.42 ± 57.33#<br>105.38 ± 2.81** | 108.13 ± 62.25##<br>106.03 ± 1.75 | 114.89 ± 65.73##<br>113.30 ± 2.55** | 117.77 ± 65.44##<br>113.19 ± 8.94** |
| Root total ginsenosides (n = 6) | 200 | 110.44 ± 71.44 | 117.29 ± 76.87###<br>106.13 ± 0.76** | 127.53 ± 78.74###<br>111.06 ± 5.41* | 133.70 ± 82.69###<br>115.91 ± 9.55** | 135.24 ± 83.14###<br>117.44 ± 8.88** |
| Stem/leave total ginsenosides (n = 6) | 200<br>200 | 95.79 ± 44.50<br>95.79 ± 44.50 | 105.83 ± 48.01###<br>105.83 ± 48.01###<br>111.48 ± 3.20 | 114.65 ± 52.81###<br>114.65 ± 52.81###<br>109.66 ± 4.02* | 123.56 ± 56.42##<br>123.56 ± 56.42##<br>115.79 ± 9.94** | 120.63 ± 55.54###<br>120.63 ± 55.54###<br>114.95 ± 7.18** |
| Total secondary ginsenosides (n = 6) | 25 | 113.94 ± 57.50 | 124.38 ± 63.82##<br>108.94 ± 2.94* | 135.95 ± 70.34##<br>110.07 ± 6.09* | 135.86 ± 65.92###<br>112.06 ± 8.89* | 131.79 ± 61.84##<br>110.42 ± 11.42* |
| Total secondary ginsenosides (n = 6) | 50 | 92.24 ± 46.30 | 98.66 ± 51.19#<br>106.71 ± 5.31* | 110.98 ± 54.98###<br>113.49 ± 9.85* | 115.63 ± 55.33###<br>119.85 ± 14.12** | 117.29 ± 57.01###<br>120.00 ± 13.48** |
| Total secondary ginsenosides (n = 6) | 100 | 80.57 ± 36.29 | 89.09 ± 39.27##<br>111.49 ± 5.86 | 97.74 ± 43.57##<br>108.54 ± 7.03 | 100.52 ± 44.64##<br>112.38 ± 8.56* | 100.78 ± 46.23##<br>112.47 ± 10.80* |

| Group | Dosage mg/kg | Before ischemia (normal value) | After ischemia (before administration of drug) Change rate (100%) | After administration of drug (min) 120 | 180 |
|---|---|---|---|---|---|
| Physiological saline (n = 6) | 3 ml | 80.55 ± 40.05 | 89.95 ± 44.44<br>112.35 ± 1.81 | 89.45 ± 44.48<br>99.50 ± 8.12 | 86.46 ± 41.55<br>98.01 ± 5.12 |
| Diltiazem (n = 6) | 5 | 92.07 ± 46.98 | 101.82 ± 54.71#<br>110.34 ± 4.17 | 119.15 ± 65.51##<br>116.97 ± 7.33** | 112.10 ± 60.59##<br>112.21 ± 6.46** |
| Di'ao Xinxuekang (n = 6) | 200 | 96.17 ± 53.08 | 101.42 ± 57.33#<br>105.38 ± 2.81** | 119.80 ± 64.02##<br>117.06 ± 11.85* | 113.36 ± 60.08###<br>111.59 ± 7.95** |
| Root total ginsenosides (n = 6) | 200 | 110.44 ± 71.44 | 117.29 ± 76.87###<br>106.13 ± 0.76** | 129.37 ± 80.37##<br>111.77 ± 12.97 | 124.35 ± 75.67##<br>109.03 ± 8.94* |
| Stem/leave total ginsenosides (n = 6) | 200<br>200 | 95.79 ± 44.50<br>95.79 ± 44.50 | 105.83 ± 48.01###<br>105.83 ± 48.01###<br>111.48 ± 3.20 | 117.05 ± 54.41##<br>117.05 ± 54.41##<br>112.88 ± 8.61* | 117.79 ± 56.25#<br>117.79 ± 56.25#<br>114.09 ± 17.39 |
| Total secondary ginsenosides (n = 6) | 25 | 113.94 ± 57.50 | 124.38 ± 63.82##<br>108.94 ± 2.94* | 131.63 ± 63.45##<br>108.64 ± 9.96 | 124.93 ± 60.68#<br>103.71 ± 9.24 |
| Total secondary ginsenosides (n = 6) | 50 | 92.24 ± 46.30 | 98.66 ± 51.19#<br>106.71 ± 5.31* | 115.60 ± 57.54###<br>120.60 ± 10.18** | 108.23 ± 52.50##<br>113.52 ± 9.17** |
| Total secondary ginsenosides (n = 6) | 100 | 80.57 ± 36.29 | 89.09 ± 39.27##<br>111.49 ± 5.86 | 102.45 ± 47.39#<br>113.48 ± 16.72 | 97.91 ± 43.69#<br>108.57 ± 13.08 |

Note:
being compared with the results before the administration of drug:
P < 0.05
P < 0.01
P < 0.001; being compared with the results in the control group:
*P < 0.05,
**P < 0.01

Test Example 4

Effects on Heart Failure Induced by Sodium Pentobarbital in Rats 50 male healthy SD rats weighting 250-350 g were randomly divided into 5 groups: control group (administered with the same volume of solvent as control), root total ginsenosides group (200 mg/Kg), groups of total secondary ginsenosides at high, middle and low dosages (200, 100, 50 mg/kg, respectively). The rats were administered through intragastric infusion, continuously for 7 days, wherein each group had 10 rats, and the volume of the administered drug was 5 ml/kg.

Each rat was anesthetized with 3% sodium pentobarbital, operated to separate right common carotid artery and left femoral artery and vein, performed arterial cannulation, and connected with pressure sensors of an eight-channel physiograph. Electrocardiographic II Lead was connected. The normal values of the following indexes were recorded: left ventricular systolic pressure (LVSP), dP/dt, t-dP/dt, systolic arterial blood pressure (SBP), arterial diastolic blood pressure (DBP), heart rate (HR). 0.5 ml of 3% sodium pentobarbital was instillated at 0.15 ml/min by using micro infusion apparatus, then 3-5 ml of 0.2% sodium pentobarbital was instillated at 0.15 ml/min until the arterial pressure decreased to 50% and dP/dt decreased to about 30%, the rat was kept for 10 minutes to induce heart failure, and the indexes under heart failure were recorded. The test drug was administered to the rats via duodenum for 15 minutes, and the indexes at 20, 30, 45, 60 and 90 minutes after the administration of drug were recorded. The standard deviations of the mean value for each index was calculated, and t-test was performed between each time-point and the control group to determine the significance of differences.

Results:
1. Effects on LVSP of rats with heart failure induced by sodium pentobarbital The results in Table 5 indicated that the root total ginsenosides could result in significant increase in LVSP within 45-90 minutes; the LVSP of animals with heart failure in the groups administered with the total secondary ginsenosides all increased within 20-90 minutes after the administration of the drug, and as compared to the control group, the result at each time point exhibited significant difference ($P<0.05$, $P<0.0$). The action at higher dosage was quick, persistent and intensive, indicating that the total secondary ginsenosides can enhance the contraction force of the left ventricle, enhance the blood ejection, and facilitate the recovery of cardiac function; and it was shown that at the same dosage, the duration of the action of the total secondary ginsenosides was longer than that of the root total ginsenosides, and the intensive action was higher than that of the root total ginsenosides.

2. Effects on SBP of rats with heart failure induced by sodium pentobarbital The results in Table 6 showed that, after the administration, the total secondary ginsenosides at 50-200 mg/kg could elevate SBP value during different time periods ($P<0.05$ or $P<0.01$), and in the 200 mg/kg dosage group, significant effects could be achieved within 30-90 minutes, they were superior to the root total ginsenosides at the same dosage in terms of the intensity and duration of action.

3. Effects on DBP of rats with heart failure induced by sodium pentobarbital The results in Table 7 showed that after administration, the DBP in the groups administered with the total secondary ginsenosides at different dosages of 50-200 mg/kg all increased, and as compared to the control group, the increase in the group of high dosage exhibited significant difference ($P<0.05$, $P<0.01$) within 30-90 minutes. The middle and low dosage groups showed increase to a certain extent, but had no significant difference in comparison with the control group. The root total ginsenosides also resulted in significant increase in DBP within 60-90 minutes.

The above results indicated that the total secondary ginsenosides could enhance the contraction force of the left ventricle, enhance the blood ejection, improve the cardiac function, alleviate the heart failure, and the action intensity and duration of the total secondary ginsenosides were superior to the root total ginsenosides at the same dosage.

TABLE 5

Effects on LVSP of rats with heart failure induced by sodium pentobarbital

| Time-point | Solvent control | Root total ginsenosides 200 mg/kg | Total secondary ginsenosides 200 mg/kg | Total secondary ginsenosides 100 mg/kg | Total secondary ginsenosides 50 mg/kg |
|---|---|---|---|---|---|
| Normal | 21.34 ± 1.57 | 20.75 ± 1.60 | 22.10 ± 1.42 | 22.68 ± 1.45 | 21.13 ± 1.80 |
| Heart failure | 10.98 ± 1.16 | 12.39 ± 3.66 | 10.29 ± 2.20 | 11.17 ± 1.19 | 11.15 ± 1.96 |
| After the end of administration | 10.05 ± 1.45 | 12.29 ± 2.15 | 11.88 ± 1.97 | 11.65 ± 1.65 | 11.38 ± 1.50 |
| 20 min | 10.11 ± 1.43 | 12.99 ± 1.64 | 12.37 ± 1.90** | 11.92 ± 1.57 | 11.53 ± 1.36 |
| 30 min | 10.10 ± 1.38 | 13.45 ± 1.59 | 12.97 ± 1.44** | 12.43 ± 1.40** | 11.95 ± 1.13 |
| 45 min | 10.20 ± 1.36 | 14.03 ± 1.21** | 14.98 ± 1.46** | 13.13 ± 1.15** | 12.18 ± 1.06** |
| 60 min | 10.24 ± 1.44 | 14.28 ± 1.15** | 15.82 ± 1.52** | 14.08 ± 0.93** | 12.77 ± 1.52** |
| 90 min | 10.37 ± 1.44 | 14.23 ± 1.25** | 16.22 ± 1.59** | 14.98 ± 1.35** | 12.65 ± 1.46** |

Note:
in comparison with the control group,
*P < 0.05,
**P < 0.01

TABLE 6

Effects on SBP of rats with heart failure induced by sodium pentobarbital

| Time-point | Solvent control | Root total ginsenosides 200 mg/kg | Total secondary ginsenosides 200 mg/kg | Total secondary ginsenosides 100 mg/kg | Total secondary ginsenosides 50 mg/kg |
|---|---|---|---|---|---|
| Normal | 20.12 ± 1.46 | 19.41 ± 1.65 | 20.14 ± 2.86 | 18.97 ± 4.08 | 17.39 ± 1.74 |
| Heart failure | 9.12 ± 2.10 | 8.89 ± 2.20 | 8.79 ± 2.61 | 8.68 ± 4.69 | 8.47 ± 3.01 |
| After the end of administration | 9.55 ± 2.24 | 9.19 ± 2.37 | 9.65 ± 2.15 | 9.31 ± 2.49 | 9.04 ± 2.77 |
| 20 min | 9.71 ± 2.21 | 9.66 ± 2.47 | 10.84 ± 2.29 | 10.59 ± 1.95 | 9.01 ± 2.56 |
| 30 min | 9.50 ± 2.22 | 9.96 ± 2.11 | 12.60 ± 2.42* | 10.64 ± 1.48 | 9.01 ± 2.74 |
| 45 min | 9.86 ± 2.32 | 10.84 ± 1.71 | 12.95 ± 2.54* | 11.13 ± 0.95 | 9.04 ± 2.33 |
| 60 min | 9.82 ± 2.66 | 12.53 ± 1.52* | 13.78 ± 2.53** | 12.60 ± 0.77* | 10.27 ± 3.08 |
| 90 min | 10.01 ± 2.51 | 12.87 ± 2.05* | 14.07 ± 2.05** | 12.91 ± 0.77* | 11.51 ± 3.41* |

TABLE 7

Effects on DBP of rats with heart failure induced by sodium pentobarbital

| Time | Solvent control | Root total ginsenosides 200 mg/kg | Total secondary ginsenosides 200 mg/kg | Total secondary ginsenosides 100 mg/kg | Total secondary ginsenosides 50 mg/kg |
|---|---|---|---|---|---|
| Normal | 14.81 ± 1.89 | 15.23 ± 1.85 | 15.20 ± 3.37 | 14.97 ± 2.22 | 13.48 ± 1.83 |
| Heart failure | 4.51 ± 0.96 | 5.13 ± 1.83 | 4.76 ± 3.32 | 4.89 ± 1.22 | 4.77 ± 2.26 |
| After the end of administration | 4.91 ± 1.06 | 5.45 ± 2.12 | 5.38 ± 2.28 | 5.51 ± 1.91 | 4.95 ± 2.36 |
| 20 min | 4.69 ± 1.26 | 5.75 ± 2.17 | 6.07 ± 1.94 | 5.61 ± 1.23 | 5.10 ± 2.10 |
| 30 min | 5.02 ± 1.27 | 5.99 ± 1.89 | 6.82 ± 1.46* | 5.69 ± 1.56 | 5.16 ± 2.48 |
| 45 min | 5.23 ± 1.17 | 6.52 ± 1.76 | 7.90 ± 1.37** | 6.18 ± 1.73 | 5.69 ± 2.43 |
| 60 min | 5.12 ± 1.39 | 6.99 ± 1.39** | 8.12 ± 1.31** | 8.16 ± 5.25 | 5.72 ± 2.48 |
| 90 min | 5.57 ± 1.54 | 7.36 ± 1.71** | 8.95 ± 1.47** | 7.19 ± 2.05 | 6.10 ± 3.40 |

Test Example 5

Effects on Dogs with Hemorrhagic Shock

36 Healthy hybrid dogs, including both male and female, were used, and were randomly divided into 6 groups: blank control group (administered with the same volume of distilled water), a group being administered with 10 mg/kg Shenmai Injection, a group being administered with 200 mg/kg ginseng root total ginsenosides (briefly referred as root total ginsenosides), and groups being administered with high, middle and low dosages of the total secondary ginsenosides respectively (namely 200, 100, 50 mg/kg). Dogs each was anesthetized by intravenous injection of sodium pentobarbital (30 mg/kg), fixed at supine posture, and catheterized within trachea, then a eight-channel electrophysiolograph was connected. Cannulation was performed at right femoral artery, and a pressure converter was connected to measure systolic blood pressure (SBP) and diastolic blood pressure (DBP) in arteries. Right femoral vein was separated for bleeding, cannulation was performed through right common carotid artery to left ventricle, and connected with a pressure converter to measure left ventricular systolic pressure (LVSP) and left ventricular diastolic blood pressure (LVDP), and Electrocardiographic II Lead was connected. After having been stabilized, the normal values of the indexes were recorded. Bleeding was performed through right femoral vein and stopped when the mean pressure in the artery was dropped to lower than ⅔ of the normal value, i.e., a shock state, and the indexes were recorded after having been stabilized. An incision of about 4 cm was made at right lumbar region to pull out duodenum for injection of each test drug solution (2 ml/kg), and then the incision was sutured. The indexes were recorded at 10, 20, 30, 40, 60, 90 and 120 minutes after the administration of drug.

Results:

The results in Table 8 showed that, in comparison with the control group, the Shenmai Injection group at various time points within 30-120 minutes, the high dosage group of total secondary ginsenosides at various time points within 30-120 minutes, and the middle dosage group of total secondary ginsenosides at various time points within 60-120 minutes exhibited significant differences (P<0.05, P<0.01); and in comparison with the root total ginsenosides, the high and middle dosage groups of the total secondary ginsenosides exhibited significant effects in increasing blood pressure (P<0.05).

The results in Table 9 showed that at all the time points, the arterial diastolic blood pressure of the groups administered with drug was higher than that of the control group; in comparison with the control group, the Shenmai Injection group at various time points within 40-120 minutes, the root total ginsenosides group at various time points within 60-120 minutes, the high dosage group of total secondary ginsenosides at various time points within 20-120 minutes, and the middle dosage group of total secondary ginsenosides at various time points within 40-120 minutes exhibited significant differences (P<0.05 or P<0.01); and in comparison with the group of root total ginsenosides, the groups of the total secondary ginsenosides at the high and middle dosages exhibited significantly superior effects in increasing the blood pressure (P<0.05).

The results in Table 10 showed that, at all time points, the left ventricular systolic pressure of the groups being administered with drug was higher than that of the control group; in comparison with the control group, the Shenmai Injection group at various time points within 30-120 minutes, the root total ginsenosides group at various time points within 40-120 minutes, the high dosage group of total secondary ginsenosides at various time points within 20-120 minutes, the middle dosage group of total secondary ginsenosides at different time points within 30-120 minutes, and the low dosage group of total secondary ginsenosides at various time points within 60-120 minutes exhibited significant differences (P<0.05, P<0.01, P<0.01). In comparison with the group being administered with the root total ginsenosides, the high dosage group of the total secondary ginsenosides exhibited higher left ventricular systolic pressure, with significant difference at the time points of 20 and 30 minutes (P<0.05), and the middle dosage group exhibited a left ventricular systolic pressure equivalent to that of the root total ginsenosides group.

The results in Table 11 showed that, at all the time points, the left ventricular diastolic pressure of each group being administered with drug was lower than that of the control group. In comparison with the control group, the Shenmai Injection group and the root total ginsenosides group at various time points within 40-120 minutes, the high and middle dosage groups of total secondary ginsenosides at various time points within 30-120 minutes, and the low dosage group of total secondary ginsenosides at the time points of 90 and 120 minutes exhibited significant differences (P<0.01 or P<0.01). And in comparison with the group of root total ginsenosides, the high dosage group of the total secondary ginsenosides exhibited lower left ventricular diastolic pressure, with significant difference at time points of 20 and 30 minutes (P<0.05), and the middle dosage group exhibited a left ventricular diastolic pressure equivalent to that of the root total ginsenosides group.

The above results indicated that the total secondary ginsenosides had an activity of improving hemodynamics such as increasing blood pressure, and exhibited significantly therapeutic effects on hemorrhagic shock. The total secondary ginsenosides functioned quicker and more intensively than the root total ginsenosides.

TABLE 8

Effects of total secondary ginsenosides on arterial systolic pressure in anesthetized dogs as hemorrhagic shock models ($\bar{x} \pm s$), unit: kPa

| Time-point | Control group | Shenmai Injection (10 mg/kg) | Root total ginsenosides (200 mg/kg) | High dosage (200 mg/kg) | Middle dosage (100 mg/kg) | Low dosage (50 mg/kg) |
|---|---|---|---|---|---|---|
| Before shock | 19.57 ± 0.73 | 19.28 ± 1.02 | 21.04 ± 1.54 | 19.25 ± 2.33 | 17.82 ± 2.07 | 18.11 ± 2.65 |
| After shock | 13.60 ± 1.56 | 13.25 ± 1.39 | 12.37 ± 1.31 | 12.67 ± 2.49 | 11.75 ± 1.44 | 12.24 ± 1.35 |
| 10 min | 13.74 ± 1.44 | 12.61 ± 1.32 | 12.43 ± 1.25 | 13.85 ± 1.78 | 12.61 ± 1.37 | 12.68 ± 0.92 |
| 20 min | 13.45 ± 1.57 | 13.62 ± 1.31 | 12.55 ± 1.42 | 15.74 ± 2.10# | 14.21 ± 1.33 | 12.80 ± 1.27 |
| 30 min | 13.59 ± 1.37 | 15.22 ± 1.63* | 13.01 ± 1.20 | 16.03 ± 2.86*# | 14.64 ± 1.30 | 13.19 ± 1.17 |
| 40 min | 13.60 ± 1.75 | 16.09 ± 1.53* | 13.58 ± 1.39 | 16.63 ± 2.52*# | 14.78 ± 1.53 | 13.19 ± 1.33 |
| 60 min | 13.16 ± 1.96 | 16.09 ± 1.53* | 13.99 ± 1.30 | 16.92 ± 2.72*# | 15.65 ± 1.14* | 13.34 ± 1.74 |
| 90 min | 13.60 ± 2.06 | 16.38 ± 1.50* | 14.82 ± 1.61 | 17.50 ± 3.17** | 15.80 ± 1.12* | 13.34 ± 1.51 |
| 120 min | 13.89 ± 2.09 | 16.96 ± 1.63** | 15.90 ± 1.70* | 17.21 ± 2.65** | 15.94 ± 1.23* | 14.07 ± 1.42 |

Note:
t-test between groups, in comparison with the control group,
*P < 0.05,
**P < 0.01; in comparison with the root total ginsenosides group,
P < 0.05,
P < 0.01 (similarly hereinafter)

TABLE 9

Effects of total secondary ginsenosides on arterial diastolic pressure in anesthetized dogs as hemorrhagic shock models ($\bar{x} \pm s$), unit: kPa

| Time-point | Control group | Shenmai Injection (10 mg/kg) | Root total ginsenosides (200 mg/kg) | High dosage (200 mg/kg) | Middle dosage (100 mg/kg) | Low dosage (50 mg/kg) |
|---|---|---|---|---|---|---|
| Before shock | 12.98 ± 1.23 | 13.19 ± 1.02 | 15.02 ± 1.80 | 14.14 ± 2.82 | 13.04 ± 1.78 | 12.65 ± 1.28 |
| After shock | 8.89 ± 1.62 | 7.25 ± 1.19 | 9.41 ± 0.90 | 9.18 ± 1.52 | 8.71 ± 1.64 | 8.98 ± 1.88 |
| 10 min | 9.04 ± 1.44 | 8.55 ± 1.02 | 9.42 ± 0.99 | 10.20 ± 1.94 | 9.29 ± 1.90 | 8.98 ± 1.88 |
| 20 min | 9.04 ± 1.44 | 9.33 ± 0.67 | 9.56 ± 0.85 | 12.10 ± 2.07*# | 10.44 ± 1.19 | 9.18 ± 1.76 |
| 30 min | 9.33 ± 1.83 | 10.15 ± 0.90 | 9.98 ± 0.89 | 12.66 ± 2.24*# | 10.87 ± 1.37 | 9.42 ± 1.86 |
| 40 min | 9.04 ± 1.73 | 10.93 ± 0.55* | 10.60 ± 1.28 | 13.27 ± 2.38**# | 11.60 ± 1.78* | 10.01 ± 1.69 |
| 60 min | 9.33 ± 1.56 | 10.87 ± 0.48* | 11.49 ± 1.68* | 13.41 ± 2.33** | 12.33 ± 1.48** | 9.86 ± 1.53 |
| 90 min | 9.48 ± 1.63 | 11.30 ± 0.27* | 11.78 ± 1.55* | 13.85 ± 2.49** | 12.03 ± 1.81* | 10.16 ± 1.80 |
| 120 min | 9.62 ± 1.67 | 11.88 ± 0.71* | 12.17 ± 2.19* | 13.83 ± 2.06** | 12.32 ± 1.98* | 10.16 ± 1.80 |

Note: t-test between groups, in comparison with the control group,
*P < 0.05,
**P < 0.01; in comparison with the root total ginsenosides group,
P < 0.05

TABLE 10

Effects of total secondary ginsenosides on left ventricular systolic pressure in anesthetized dogs as hemorrhagic shock models ($\bar{x} \pm s$), unit: kPa

| Time-point | Control group | Shenmai Injection (10 mg/kg) | Root total ginsenosides (200 mg/kg) | High dosage (200 mg/kg) | Middle dosage (100 mg/kg) | Low dosage (50 mg/kg) |
|---|---|---|---|---|---|---|
| Before shock | 24.22 ± 2.45 | 22.42 ± 2.24 | 24.37 ± 1.42 | 23.23 ± 1.62 | 23.97 ± 1.65 | 22.94 ± 0.88 |
| After shock | 15.67 ± 2.31 | 12.98 ± 2.32 | 14.87 ± 3.32 | 14.55 ± 3.45 | 15.73 ± 1.51 | 16.86 ± 2.71 |
| 10 min | 15.67 ± 2.31 | 14.87 ± 1.64 | 15.61 ± 3.40 | 17.70 ± 3.57 | 17.07 ± 1.35 | 16.86 ± 2.71 |
| 20 min | 14.54 ± 3.14 | 17.09 ± 2.39 | 15.75 ± 3.65 | 22.72 ± 3.04**## | 17.79 ± 4.17 | 16.86 ± 2.71 |
| 30 min | 14.02 ± 2.72 | 18.69 ± 2.77* | 17.40 ± 4.26 | 23.10 ± 2.17***# | 19.10 ± 4.71* | 16.86 ± 2.71 |
| 40 min | 14.84 ± 2.77 | 19.51 ± 2.53* | 19.99 ± 4.06* | 23.10 ± 2.17*** | 20.59 ± 3.85* | 18.58 ± 3.48 |
| 60 min | 14.33 ± 1.99 | 21.05 ± 1.51*** | 19.05 ± 3.39** | 22.85 ± 2.29*** | 19.90 ± 3.32** | 19.84 ± 3.41** |
| 90 min | 13.48 ± 2.34 | 21.05 ± 1.51*** | 19.73 ± 3.44** | 23.10 ± 2.17*** | 19.22 ± 2.46** | 18.47 ± 3.91* |
| 120 min | 14.65 ± 2.90 | 21.73 ± 2.05* | 20.41 ± 3.17* | 23.79 ± 3.16*** | 20.59 ± 3.85* | 20.63 ± 2.61** |

Note:

in comparison with the control group,

*P < 0.05,

**P < 0.01,

***P < 0.01; in comparison with the root total ginsenosides group,

P < 0.05,

P < 0.01

TABLE 11

Effects of total secondary ginsenosides on left ventricular diastolic pressure in anesthetized dogs as hemorrhagic shock models ($\bar{x} \pm s$), unit: kPa

| Time-point | Control group | Shenmai Injection (10 mg/kg) | Root total ginsenosides (200 mg/kg) | High dosage (200 mg/kg) | Middle dosage (100 mg/kg) | Low dosage (50 mg/kg) |
|---|---|---|---|---|---|---|
| Before shock | 1.72 ± 1.39 | 1.71 ± 0.73 | 1.73 ± 1.10 | 1.69 ± 1.47 | 1.72 ± 1.32 | 1.67 ± 1.33 |
| After shock | 4.43 ± 1.25 | 4.64 ± 0.42 | 4.47 ± 0.62 | 4.51 ± 0.52 | 4.07 ± 1.16 | 4.13 ± 1.22 |
| 10 min | 4.57 ± 1.04 | 4.05 ± 0.41 | 4.13 ± 0.94 | 4.31 ± 0.99 | 4.40 ± 1.36 | 4.26 ± 1.17 |
| 20 min | 4.72 ± 1.39 | 3.98 ± 0.98 | 4.01 ± 0.87 | 3.20 ± 1.04 | 3.72 ± 1.47 | 3.87 ± 1.28 |
| 30 min | 4.57 ± 1.04 | 3.97 ± 0.45 | 3.87 ± 1.45 | 2.90 ± 0.69*** | 2.58 ± 1.56** | 3.73 ± 1.29 |
| 40 min | 4.28 ± 0.45 | 2.96 ± 0.52*** | 2.86 ± 0.74*** | 2.24 ± 0.72*** | 2.56 ± 1.68** | 3.73 ± 1.29 |
| 60 min | 4.15 ± 0.74 | 1.95 ± 0.43*** | 1.83 ± 0.37*** | 1.81 ± 0.34*** | 2.05 ± 1.01*** | 3.32 ± 1.02 |
| 90 min | 4.14 ± 0.44 | 1.82 ± 0.17*** | 1.72 ± 0.93*** | 1.65 ± 0.61*** | 2.02 ± 1.54*** | 2.91 ± 0.86*** |
| 120 min | 4.48 ± 0.41 | 1.81 ± 0.11*** | 1.69 ± 0.99*** | 1.24 ± 0.83*** | 1.80 ± 1.31*** | 2.27 ± 1.23*** |

Note:

in comparison with the control group,

**P < 0.01,

***P < 0.001

Test Example 6

Effects on Arrhythmia in Rats

70 SD rats, including half male and half female, were randomly divided into: control group, Diltiazem group, 200 mg/kg Di'ao Xinxuekang group, 200 mg/kg the root total ginsenosides group, and 200, 100, 50, 25 mg/kg dosage groups of the total secondary ginsenosides. On the $7^{th}$ day of administration of drug, 30 minutes after the administration of drug, each of the rats was anesthetized by intraperitoneal injection of 300 mg/kg 10% chloral hydrate, fixed in supine position on rat bench. The chart speed was set at 50 mm/s, and the sensitivity was set at 20 mm/mv. After printing under standard voltage, normal II Lead electrocardiogram was recorded for a certain period, then the rat was administered-with 4 mg/kg barium chloride via sublingual vein and observed immediately to record the electrocardiograms at 1, 5, 10, 15, 20, 25, 30 minutes after the administration of barium chloride. The heart rate was calculated and compared with the reference value before administration, and the onset time and time period of arrhythmia were compared as well. The incidence rates of ventricular premature beat (VP), ventricular tachycardia (VT) and ventricular fibrillation (VF) were calculated.

Results:

The results in Table 12 showed that all the groups presented significant reduction in heart rate after the injection of $BaCl_2$, the heart rate was gradually regained 10 minutes after the administration of the total secondary ginsenosides at 200 mg/kg, 30 minutes after the administration of the total secondary ginsenosides at 100 mg/kg, and 20 minutes after the administration of the root total ginsenosides at the dosage of 200 mg/kg.

The results in Table 13 showed that the total secondary ginsenosides at the dosage of 50-200 mg/kg could significantly delay the onset time of VP, VT of arrhythmia ($P<0.05$, $P<0.01$), significantly shorten the duration of arrhythmia ($P<0.05$, $P<0.01$), and could significantly reduce the incidence rate of VF ($P<0.05$); the root total ginsenosides at 200 mg/kg could significantly delay the onset time of VP, VT of arrhythmia ($P<0.05$), could significantly shorten the duration of arrhythmia ($P<0.01$), with a function pattern similar to the total secondary ginsenosides at 100 mg/kg.

The above results showed that the total secondary ginsenosides could significantly improve the arrhythmia induced by $BaCl_2$, inhibit the incidence rate of ventricular fibrillation (VF), and exhibit better effects than the root total ginsenosides at the same dosage.

TABLE 12

Heart rate (beat/min) changes in the groups after intravenous injection of $BaCl_2$ ($\overline{X} \pm S$, n = 10)

| Group | Dosage (mg/kg) | $BaCl_2$ Before | $BaCl_2$ After 5 min | $BaCl_2$ After 10 min | $BaCl_2$ After 20 min | $BaCl_2$ After 30 min |
|---|---|---|---|---|---|---|
| Blank control | — | 473 ± 28 | 283 ± 39** | 279 ± 26** | 283 ± 60** | 290 ± 58** |
| Diltiazem | 50 | 397 ± 53 | 327 ± 64* | 360 ± 88 | 381 ± 71 | 399 ± 42 |
| Di'ao Xinxuekang | 200 | 464 ± 38 | 314 ± 52** | 325 ± 58** | 416 ± 66 | 431 ± 42 |
| Root total ginsenosides | 200 | 458 ± 47 | 320 ± 81** | 316 ± 77** | 456 ± 38 | 451 ± 45 |
| Total secondary ginsenosides | 200 | 443 ± 28 | 235 ± 86** | 368 ± 75 | 394 ± 82 | 423 ± 45 |
| | 100 | 464 ± 29 | 319 ± 84** | 345 ± 71** | 419 ± 55* | 441 ± 37 |
| | 50 | 469 ± 41 | 312 ± 74** | 300 ± 34** | 362 ± 96** | 431 ± 66 |
| | 25 | 438 ± 40 | 265 ± 17** | 264 ± 24** | 257 ± 22** | 359 ± 72** |

Note:
Comparison between each time point in each group and before the administration of barium chloride (*$P < 0.05$, **$P < 0.01$)

TABLE 13

Protection effects of the total secondary ginsenosides on rat arrhythmia induced by $BaCl_2$ ($\overline{X} \pm S$, n = 10)

| Group | Dosage (mg/kg) | Incidence rate of VF (%) | Onset time of VP (s) | Onset time of VT (s) | Duration of arrhythmia (min) |
|---|---|---|---|---|---|
| Blank control | — | 90 | 4.3 ± 5.1 | 7.0 ± 6.7 | 32.2 ± 4.9 |
| Diltiazem | 50 | 0* | 15.0 ± 10.8** | 20 ± 8.8** | 13.2 ± 6.0** |
| Di'ao Xinxuekang | 200 | 40 | 10.0 ± 5.5* | 12.9 ± 5.2* | 19.3 ± 6.8** |
| Root total ginsenosides | 200 | 30 | 13.4 ± 8.2* | 16.4 ± 7.9* | 19.6 ± 3.1** |
| Total secondary ginsenosides | 200 | 10* | 14.8 ± 4.7** | 18.5 ± 4.1** | 14.7 ± 1.5** |
| | 100 | 10* | 13.3 ± 2.3** | 16.8 ± 2.1** | 16.8 ± 2.7* |
| | 50 | 20* | 10.0 ± 2.8* | 11.8 ± 10.9* | 19.9 ± 3.5* |
| | 25 | 30 | 5.8 ± 7.1 | 7.5 ± 8.2 | 28.7 ± 3.6 |

Test Example 7

Effects on Thrombosis In Vivo

70 Rats, half male and half female, weighting 250-300 g, were randomly divided into 7 groups, 10 rats per group, and fed for one week in advance. The said 7 groups included high, middle and low dosage groups of the total secondary ginsenosides (200, 100 and 50 mg/kg), and control groups: Diltiazem group (50 mg/kg), Di'ao Xinxuekang group (200 mg/kg), root total ginsenosides group (200 mg/kg) and blank control group (water). administered All the drugs and controls were administered through intragastrical perfusion for 7 days.

Measurement of the rate for inhibition of thrombosis: on the 7$^{th}$ day after administration of drug, 30 minutes after the administration, each of rats was anesthetized with sodium pentobarbital, the left external jugular vein and right common carotid artery were separated, three segments of polyethylene tubes were used to form cannula, and then 5 cm weighed 4-suture was placed in the middle segment. These polyethylene tubes were filled with heparin-physiological saline (50 U/ml). When one end of the tube was inserted into the external jugular vein, one end of the tube was clamped and the end fixed by suture was inserted into the right common carotid artery. After this operation, bleeding was performed immediately and then stopped 15 minutes later, the suture was taken out quickly and weighed. The wet weight of thrombus was calculated by subtracting the suture weight from the total weight. The thrombosis inhibition rate was calculated according to the following formula.

Inhibition rate (%)=[(Thrombus weight of the control group)−(Thrombus weight of the group administered with drug)]/(Thrombus weight of the control group)×100%

Results:

The results were shown in Table 14, indicating that the total secondary ginsenosides (100-200 mg/kg) could significantly inhibit the thrombosis in rat jugular arteriovenous bypass (P<0.05) with a maximum inhibition rate of 29%. The root total ginsenosides (200 mg/kg) exhibited a tendency of inhibiting thrombosis but did not show significant difference, the inhibition rate being 16%. The control drugs, Diltiazem and Di'ao Xinxuekang, both exhibited significant inhibition effects on thrombosis (P<0.05), with an inhibition rate of 33% and 23%, respectively.

The above results indicated that the total secondary ginsenosides (100-200 mg/kg) exhibited significant inhibition effects on the thrombosis in experimental rat jugular arteriovenous bypass, and were significantly superior to the root total ginsenosides (200 mg/kg).

TABLE 14

Inhibition effects of the total secondary ginsenosides on the thrombosis in experimental rat jugular arteriovenous bypass

| Group | Dosage (mg/kg) | Number of animals | Wet weight of thrombus (g) | Inhibition rate (%) |
|---|---|---|---|---|
| Blank control | — | 10 | 0.0298 ± 0.006 | |
| Diltiazem | 50 | 10 | 0.0200 ± 0.005* | 32.89 |
| Di'ao Xinxuekang | 200 | 10 | 0.0229 ± 0.005* | 23.15 |
| Root total ginsenosides | 200 | 10 | 0.0251 ± 0.009 | 15.77 |
| Total secondary | 200 | 10 | 0.0211 ± 0.004* | 29.19 |
| ginsenosides | 100 | 10 | 0.0227 ± 0.007* | 23.83 |
|  | 50 | 10 | 0.0267 ± 0.010 | 10.40 |

Note:
in comparison with the control group,
*P < 0.05,
** P < 0.01

INDUSTRIAL APPLICABILITY

In the present invention, modern pharmaceutical techniques were employed for the manufacture of total secondary ginsenosides from *panax* plants by extraction, said total secondary ginsenosides contain ginsenosides Rg2, Rg3, Rh1 as main components. It showed in the pharmacodynamic tests that:

1. The total secondary ginsenosides exhibited significant improvement on acute myocardial ischemia in dogs, and thus significantly alleviated the degree of myocardial ischemia, as measured by epicardial electrogram (Σ-ST);
2. The total secondary ginsenosides reduced the infarction zone area as showed by N-BT staining; significantly increased the coronary blood flow during myocardial ischemia, promoted the opening and establishment of bypass circulation, and increased the oxygen supply to cardiac muscle;
3. The total secondary ginsenosides could significantly elevate the level of 6-Keto-PGF$_{1\alpha}$ in blood plasma and the ratio of 6-Keto-PGF$_{1\alpha}$/TXB$_2$ during myocardial ischemia;
4. The total secondary ginsenosides exhibited very significant function against cardiac shock. At the same dosages, total secondary ginsenosides started to act about 20 minutes after the administration, while the total ginsenosides started to act about 40 minutes after the administration with relatively weak effects. The total secondary ginsenosides were superior to the total ginsenosides in terms of the rate and effects of action;
5. The total secondary ginsenosides could significantly enhance the contraction force of left ventricle, enhance blood ejection, improve the cardiac function, and alleviate heart failure. The total secondary ginsenosides were superior to the root total ginsenosides at the same dosages in terms of the intensity and duration of action;
6. As for the arrhythmia induced by BaCl$_2$ in rats, the total secondary ginsenosides at 200 mg/kg could significantly delay the onset time of VP and VT, and significantly shorten the duration of arrhythmia;
7. The pre-administration of total secondary ginsenosides at 200 mg/kg administered for 7 days inhibited the formation of thrombosis in rat jugular arteriovenous bypass;
8. The total secondary ginsenosides inhibited the aggregation of platelets induced by ADP. In particular, the total secondary ginsenosides exhibited significant inhibition effects on the platelet aggregation in vitro in the high dosage group.

Based on the traditional Chinese medical theory and the research results in pharmacodynamics tests, a novel drug comprising total secondary ginsenosides as the main ingredients was developed for treatment of deficiency of heart-YANG, deficiency of heart-energy, and thoracic obstruction heart pain induced by qi stagnation blood stasis. For patients' convenience, oral tablets were developed.

Evaluation of Toxicity:

The maximum dosage of the total secondary ginsenosides intragastrically administered to mice was 8 g/kg.

The pharmaceutical composition of total secondary ginsenosides according to the present invention, for example the oral disintegrating tablets, can be administered as follows:

Buccal administration: 3 times per day, each 1-2 tablets;

Cautions:
1. It should be used at the specified usage and dosage according to the instructions of a doctor.
2. It should not be used in combination with Rhizoma et Radix Veratri.
3. It is not suitable for patient catching a cold or having a fever.

What is claimed is:

1. A pharmaceutical composition of total secondary ginsenosides, comprising total secondary ginsenosides which is an extract of total secondary ginsenosides extracted from a plant of *Panax*, said extract comprises the following components:
    A. Ginsenosides with protopanaxadiol as aglycone, including ginsenoside-Rg3;
    B. Ginsenosides with protopanaxatriol as aglycone, including ginsenoside-Rg2 and ginsenoside-Rh1;
    wherein said ginsenoside Rg3 is ginsenoside 20-(S)-Rg3 and/or ginsenoside 20-(R)-Rg3;
    said ginsenoside Rg2 is ginsenoside 20-(S)-Rg2 and/or ginsenoside 20-(R)-Rg2;
    said ginsenoside Rh1 is ginsenoside 20-(S)-Rh1 and/or ginsenoside 20-(R)-Rh1;
    said ginsenoside Rg3 is 12-20%, said ginsenoside Rg2 is 4-16%, and said ginsenoside Rh1 is 3-5% by weight; and the total amount of ginsenosides with protopanaxadiol or protopanaxatriol as aglycone is 50%-98% by weight.

2. A process for preparing a pharmaceutical composition of total secondary ginsenosides according to claim 1, comprising the following steps:
    (1) Preparation of an extract liquid of total ginsenosides: extracting a plant of *Panax* with water or an organic solvent, then concentrating the resulting extract liquid;
    (2) Preparation of a hydrolyzate liquid: hydrolyzing the said concentrated extract liquid in the presence of an inorganic or organic acid as catalyst;
    (3) Absorption with resin: passing the hydrolyzate liquid through a macroporous resin for absorption on column;
    (4) Removal of impurities: eluting the absorption column that has absorbed the hydrolyzate liquid with water, an alkaline aqueous solution, ethanol at a concentration below 35%, to remove impurities;
    (5) Elution, concentration, and drying: after the removal of impurities, eluting the absorption column with ethanol at a concentration of above 35%, collecting the eluant eluted by ethanol at a concentration of above 35%, concentrating the eluant to obtain a liquid extract, and drying the said liquid extract under vacuum, resulting in the said pharmaceutical composition of total secondary ginsenosides;
    wherein the inorganic or organic acid catalyst being used in the step (2) is selected from the group consisting of glacial acetic acid, propionic hydrochloric acid, and sulfuric acid; the hydrolysis is performed at 80-100° C for 3-8 hours; the macroporous resin used in the step (3) is a styrene type macroporous resin, including styrene type macroporous resins, ethyl-styrene type macroporous resins, methyl-styrene type macroporous resins; the alkaline aqueous solution used in the step (4) is an aqueous solution formed by a compound selected from sodium hydroxide, potassium hydroxide, sodium carbonate, potassium carbonate at a concentration of 0.1-5.0%; the ethanol used for eluting the absorption column in the step (5) has a concentration of 60-80%.

3. The process for preparing a pharmaceutical composition of total secondary ginsenosides according to claim 2, wherein the ethanol used in the step (4) for removal of impurities has a concentration of 15-25%.

4. A dosage form comprising a therapeutically effective amount of a pharmaceutical composition of total secondary ginsenosides according to claim 1, an additive, an excipient and a pharmaceutically acceptable carrier.

5. An oral disintegrating tablet, comprising a therapeutically effective amount of a pharmaceutical composition of total secondary ginsenosides according to claim 1.

6. A method for treatment of angina pectoris of coronary heart disease, comprising administering a patient suffering from angina pectoris of coronary heart disease with the pharmaceutical composition of total secondary ginsenosides according to claim 1.

7. A method for treatment of myocardial ischemia, comprising administering a patient suffering from myocardial ischemia with the pharmaceutical composition of total secondary ginsenosides according to claim 1.

8. A method for treatment of hemorrhagic shock, comprising administering a patient suffering from hemorrhagic shock with the pharmaceutical composition of total secondary ginsenosides according to claim 1.

9. A method for treatment of heart failure, comprising administering a patient suffering from heart failure with the pharmaceutical composition of total secondary ginsenosides according to claim 1.

10. A method for treatment of arrhythmia, comprising administering a patient suffering from arrhythmia with the pharmaceutical composition of total secondary ginsenosides according to claim 1.

* * * * *